(12) United States Patent
Faull et al.

(10) Patent No.: US 6,441,004 B1
(45) Date of Patent: Aug. 27, 2002

(54) MONOCYTE CHEMOATTRACTANT PROTEIN-1 INHIBITOR COMPOUNDS

(75) Inventors: Alan Wellington Faull; Andrew John Barker; Jason Grant Kettle, all of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/485,061

(22) PCT Filed: Aug. 4, 1998

(86) PCT No.: PCT/GB98/02341

§ 371 (c)(1),
(2), (4) Date: Feb. 3, 2000

(87) PCT Pub. No.: WO99/07351

PCT Pub. Date: Feb. 18, 1999

(30) Foreign Application Priority Data

Aug. 7, 1997 (GB) ............................................... 9716657

(51) Int. Cl.$^7$ ..................... A61K 31/404; C07D 209/42; C07D 401/04; C07D 409/04; C07D 409/06

(52) U.S. Cl. ....................... 514/339; 514/415; 514/418; 514/419; 514/444; 546/277.4; 548/490; 548/491

(58) Field of Search ................................. 514/415, 418, 514/419, 339, 444; 548/490, 491; 546/277.4

(56) References Cited

U.S. PATENT DOCUMENTS

| | | | |
|---|---|---|---|
| 3,557,142 A | 1/1971 | Bell .................... | 260/326.13 |
| 3,776,923 A | 12/1973 | Remers et al. .......... | 260/326.16 |
| 3,997,557 A | 12/1976 | Helsley et al. ....... | 260/326.12 R |
| 4,529,724 A | 7/1985 | Ho ....................... | 514/215 |
| 4,608,384 A | 8/1986 | Wierzbicki et al. ...... | 514/413 |
| 4,721,725 A | 1/1988 | Biller et al. ............ | 514/412 |
| 4,751,231 A | 6/1988 | Halczenko et al. ....... | 514/412 |
| 4,965,369 A | 10/1990 | Maetzel et al. .......... | 548/492 |
| 5,081,145 A | 1/1992 | Guindon et al. ......... | 514/419 |
| 5,190,968 A | 3/1993 | Gillard et al. ............ | 514/419 |
| 5,254,563 A | 10/1993 | Huth et al. .............. | 514/292 |
| 5,272,145 A | 12/1993 | Prasit et al. ............. | 514/227.8 |
| 5,273,980 A | 12/1993 | Frenette et al. ......... | 514/300 |
| 5,288,743 A | 2/1994 | Brooks et al. ........... | 514/365 |
| 5,290,798 A | 3/1994 | Gillard et al. ............ | 514/361 |
| 5,308,850 A | 5/1994 | Gillard et al. ............ | 514/301 |
| 5,389,650 A | 2/1995 | Frenette et al. ......... | 514/337 |
| 5,399,699 A | 3/1995 | Kolasa et al. ........... | 546/174 |
| 5,482,960 A | 1/1996 | Berryman et al. ........ | 514/414 |
| 5,684,032 A | 11/1997 | Elliott et al. ............. | 514/414 |
| 5,852,046 A | 12/1998 | Lang et al. ............... | 514/419 |
| 5,955,492 A | 9/1999 | Thompson et al. ........ | 514/419 |
| 6,184,235 B1 | 2/2001 | Connor et al. ............ | 514/322 |

FOREIGN PATENT DOCUMENTS

| | | |
|---|---|---|
| DE | 298 913 A5 | 3/1992 |
| EP | 0 077 029 | 4/1983 |
| EP | 0 144 014 | 7/1984 |
| EP | 0 186 367 | 7/1986 |
| EP | 0 189 690 | 8/1986 |
| EP | 0 419 049 A1 | 3/1991 |
| EP | 0 480 659 A2 | 4/1992 |
| EP | 0 535 923 A1 | 4/1993 |
| EP | 0 535 924 A1 | 4/1993 |
| EP | 0 535 925 A1 | 4/1993 |
| EP | 0 535 926 A1 | 4/1993 |
| EP | 0 639 537 A | 2/1995 |
| EP | 0 639 573 A1 | 2/1995 |
| EP | 0 822 185 A1 | 2/1998 |
| EP | 0 275 667 | 7/1998 |
| FR | 2 565 981 | 12/1985 |
| WO | WO 86/00896 | 2/1986 |
| WO | WO 93/12780 | 7/1993 |
| WO | WO 93/16069 | 8/1993 |
| WO | WO 93/20078 | 10/1993 |
| WO | WO 93/25546 | 12/1993 |
| WO | WO 94/14434 | 7/1994 |
| WO | WO 96/03377 | 2/1996 |
| WO | 96/18393 A | 6/1996 |
| WO | WO 96/18393 | 6/1996 |
| WO | WO 96/31492 | 10/1996 |
| WO | WO 96/33171 | 10/1996 |
| WO | WO 96/37467 | 11/1996 |
| WO | WO 96/37469 | 11/1996 |
| WO | WO 97/12613 | 4/1997 |
| WO | WO 97/12615 | 4/1997 |
| WO | 97/12615 A | 4/1997 |
| WO | WO 97/30704 | 8/1997 |
| WO | WO 97/35572 | 10/1997 |
| WO | WO 98/06703 | 2/1998 |
| WO | WO 99/33800 | 7/1999 |

OTHER PUBLICATIONS

Database Chemabs, Chemical Abstracts Service, Columbus, Ohio, US, STN, accession No. 125:142551, XP002094570, see abstract: RN 179526–39–7, 1996.

Berman et al., "Localization of Monocyte Chemoattractant Peptide–1 . . . Autoimmune Encephalomyelitis and Trauma in the Rat", Journal of Immunology 1996. vol. 156, pp. 3017–3023; XP002105551 cited in application, see the whole document.

Database Chemabs, Chemical Abstracts Service, Columbus, Ohio, US, AN: 119:62465, XP002105556, see abstract & Korobchenko et al., "Sythesis and antiviral activity of pyrrolecarboxylic acids and their derivatives" Khim.–Farm.ZH., vol. 26, No. 11–12, 1992, pp. 57–59, see the whole document.

(List continued on next page.)

Primary Examiner—Fiona T. Powers
(74) Attorney, Agent, or Firm—Morgan, Lewis & Bockius LLP

(57) ABSTRACT

The invention concerns the use of a compound of the formula (I) in which Z, X, T, A, $R^1$, $R^2$, p and q have any of the meanings defined herein, and their pharmaceutically acceptable salts or in vivo hydrolysable esters, in the treatment of a disease or condition mediated by monocyte chemoattractant protein-1 (MCP-1). Certain of the components of formula (I) are novel and are provided, together with pharmaceutical compositions thereof, as further features of the invention.

15 Claims, No Drawings

OTHER PUBLICATIONS

Deleuran et al., "Localization of monocyte chemotactic and activating factor (MCAF/MCP–1) in psoriasis", Journal of Dermatological Science, 1996, vol. 13(3), pp. 228–236; XP002105554 cited in the application, see the whole document.

Grimm et al., "Enhanced expression and production of monocyte chemoattractant protein–1 in inflammatory bowel disease mucosa", Journal of Leukocyte Biology, 1996, vol. 59(6) pp, 804–812; XP002105555 cited in the application, see the whole document.

Harrison et al.; "Cyclopenta[β]indoles, Part 2. [1] Model studies towards tremorgenic mycotoxins"; Journal of Chemical Society; 1995, pp. 1131–1136; XP002105550 cited in the application, see p. 1132, Scheme 3, compound 9.

Jones et al., "Potential Role of Monocyte Chemoattractant Protein 1/JE in . . . Alveolitis in the Rat", Journal of Immunology, 1992, vol. 149(6), pp. 2147–2154; XP002105552 cited in the application, see the whole document.

Koch et al., Enhanced Production of Monocyte Chemoattractant Protein –1 in Rheumatoid Arthritis, Journal of Clinical Investigation, 1992, vol. 90(3), pp. 772–779; XP002105553, cited in the application, see the whole document.

Bobsěšet al., "Synthesis of N–Phenylsulfonyl Protected Furo[3,2–β]pyrroles", Collect. Czech. Commun., vol. 59, 1994, pp. 499–205.

Chemical Abstracts, vol. 123, No. 14, Oct. 2, 1995 Columbus, Ohio, US; abstract No. 179521d, Kataoka, Kenichiro et al.: "Homopiperazines as cell migration inhibitors." Xp002081582 see abstract & JP 95 145060 A (Tejin Ltd).

Dandáet al., "Reference Data", Magnetic Resonance in Chemistry, vol. 28, 1990, pp. 830–831.

Derwent Abstract for JP 63284177 including Chemical Abstract Registry Records for specific compounds indexed 1988.

Derwent and Chemical Abstracts for International Patent Application, Publication No. WO 92/04343 1992.

Derwent World Patents Index record, JAPIO record and Chemical Abstract for Molecules (1997), 2(4), 69–79, including Chemical Abstract Registry records for specific compounds indexed.

Hartman et al., "The Synthesis of 5–alkylaminomethylthieno[2,3–b] pyrrole–5–sulfonamides", Heterocycles, vol. 29, 1989, pp. 1943–1949.

Japanese Abstract N–Phenylsulfonylindole derivatives, JP 04273857 A2 1992.

Krutoikova et al., "Condensed O–, N–Heterocycles by the Transformation of Azidoacrylates", Monatshefte für Chemie 123, 1992, pp. 807–815.

Krutošiková et al., "Derivatives fo Furo[3,2–β]pyrrole", Collect. Czech. Chem. Commun., vol. 59, 1994, pp. 473–481.

Krutošiková et al., "Reactions of Methyl 2–Formylfuor[3, 2–β]pyrrole–5–carboxylates", Chem. Papers. vol. 50, 1996, pp. 72–76.

Krutošiková et al., "Substituted Benzylfuro[3,2–β]pyrroles", Collect. Czech. Chem. Commun., vol. 57, 1992, pp. 1487–1494.

Krutošiková et al., "Substituted Vinyl Azides in Synthesis of Furo[3,2–β:4,5–β]–dipyrroles and Pyrrolo[2',3':4,5]Furo[3, 2–c]pyridines", Heterocycles. vol. 37, No. 3, 1994, pp. 1695–1700.

Krutošiková et al., "Substituted Vinyl Azides in the Synthesis of Condensed Nitrogen Heterocycles", Chem. Papers, vol. 48, 1994, pp. 268–273.

Krutošiková et al., "Synthesis and Reactions of Furo[3,2–b] pyurrole Type Aldehydes", Czech. Chem. Commun., vol. 58, 1993, pp. 2139–2149.

Murakami et al., "Direct Regioselective Vinylationof Indoles Using Palladium (II) Chloride" Heterocycles, 1984, vol. 22, No. 7, pp. 1493–1496.

Rosenmund et al., "Decarboxylierungen einiger 1–Akyl–2–carboxy–3–indolessigsäuren sowie Synthese eines 5–Thiocyanaot–2, 3–dihydroindols", Chemical Berichte, 1975, vol. 108, pp. 3538–3542, XP–00909395.

Troschütz et al., "Synthesis of Substituted 4–Amino–4–cyano–1–oxo–1,2,5,10–tetrahydorzaepinol[3, 4–b]indoles", Journal of Heterocyclic Chemistry, Sep.–Oct. 1997, vol. 34, pp. 1431–1440, XP–000909451.

Yokoyama et al., "New Synthetic Method for Dehydrotryptophan Derivatives. Synthetic Studies on Indoles and Related Compounds, XXXIV[1]", Chemical and Pharmaceutical Bulletin, 1994, vol. 42, No. 4, pp. 832–838.

Yokoyama et al., "Palladium–catalyzed cross–coupling reaction: direct allylation of aryl bromides with allyl acetate" Tetrahedron Letters., vol. 26, No. 52—1985 pp. 6457–6460, XP002081581 Oxford GB* p. 6458–6459: compound 7*.

MONOCYTE CHEMOATTRACTANT PROTEIN-1 INHIBITOR COMPOUNDS

This application is the national phase of international application PCT/GB98/02341 filed Aug. 4, 1998 which designated the U.S.

The present invention relates to anti-inflammatory compounds that act via inhibition of Monocyte Chemoattractant Protein-1 (MCP-1) and especially MCP-1 inhibitor compounds that contain an indole moiety. The invention further relates to processes for their preparation, to intermediates useful in their preparation, to their use as therapeutic agents and to pharmaceutical compositions containing them.

MCP-1 is a member of the chemokine family of pro-inflammatory cytokines which mediate leukocyte chemotaxis and activation. MCP-1 is a C-C chemokine which is one of the most potent and selective T-cell and monocyte chemoattractant and activating agents known. MCP-1 has been implicated in the pathophysiology of a large number of inflammatory diseases including rheumatoid arthritis, glomerular nephritides, lung fibrosis, restenosis (International Patent Application WO 94/09128), alveolitis (Jones et al., 1992, *J. Immunol.*, 149, 2147) and asthma. Other disease areas where MCP-1 is thought to play a part in their pathology are atherosclerosis (e.g. Koch et al., 1992, *J. Clin. Invest.*, 90, 772–779), psoriasis (Deleuran et al., 1996, *J. Dermatological Science*, 13, 228–236), delayed-type hypersensitivity reactions of the skin, inflammatory bowel disease (Grimm et al., 1996, *J. Leukocyte Biol.*, 59, 804–812), multiple sclerosis and brain trauma (Berman et al, 1996, *J. Immunol.*, 156, 3017–3023). An MCP-1 inhibitor may also be useful to treat stroke, reperfusion injury, ischemia, myocardial infarction and transplant rejection.

MCP-1 acts through the MCP-1 receptor (also known as the CCR2 receptor). MCP-2 and MCP-3 may also act, at least in part, through the MCP-1 receptor. Therefore in this specification, when reference is made to "inhibition or antagonism of MCP-1" or "MCP-1 mediated effects" this includes inhibition or antagonism of MCP-2 and/or MCP-3 mediated effects when MCP-2 and/or MCP-3 are acting through the MCP-1 receptor.

Patent Nos. U.S. 005389650A, U.S. 005290798A, EP 0535926A1, EP 0535923A1, U.S. 005190968A, EP 0535924A1, EP 0419049A1, U.S. Pat. No. 5,308,850, EP 0535925A1, WO 93/16069, WO 93/25546, U.S. 005273980A and U.S. Pat. No. 5,272,145 disclose indole compounds as inhibitors of leukotriene biosynthesis with a benzyl moiety attached to the nitrogen of the indole ring. Similar compounds are also disclosed in WO 93/20078 (severe head injury), EP 0186367 (antiallergy), EP 0275667 (inhibitors of leukotriene biosynthesis), U.S. 4965369A (process patent) WO 94/14434 (antagonizing endothelin receptors), EP 0480659 A2 (treatment of hyperuricemia) and WO 96/03377A1 (allosteric effectors at muscarinic receptors).

The present invention is based on the discovery of a class of compounds containing an indole moiety which have useful inhibitory activity against MCP-1.

Accordingly one aspect of the present invention provides the use of a compound of the formula (I) in the manufacture of a medicament for antagonising an MCP-1 mediated effect in a warm blooded animal, such as man;

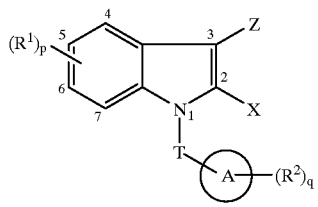

(I)

wherein:

$R^1$ is independently selected from trifluoromethyl, $C_{1-4}$alkyl, halo, hydroxy, $C_{1-4}$alkoxy, $C_{1-4}$alkanoyl, $C_{1-4}$alkanoyloxy, carboxy, trifluoromethoxy, amino, cyano, $C_{1-4}$alkylamino, di($C_{1-4}$alkyl)amino, $C_{1-4}$alkanoylamino, nitro, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—($C_{1-4}$alkyl)carbamoyl$C_{1-4}$alkyl, N—($C_{1-4}$alkyl)$_2$carbamoyl-$C_{1-4}$alkyl, hydroxy$C_{1-4}$alkyl, $C_{1-4}$alkoxy$C_{1-4}$alkyl, morpholino, pyrrolidinyl, carboxy$C_{1-4}$alkylamino, $R^3$ and —$OR^3$ (where $R^3$ is optionally substituted aryl or an optionally substituted 5- or 6- membered heteroaryl ring);

p is 0–4 and $R^1$ can have the same or different values when p is 2–4 with the proviso that no more than one $R^1$ can be chosen from the group amino, $C_{1-4}$alkylamino, di($C_{1-4}$alkyl)amino, morpholino and pyrrolidinyl;

T is of the formula

where $R^4$ is independently selected from hydrogen or $C_{1-4}$alkyl and m=1–3 and $R^4$ can have different values when m is 2 or 3;

X is $CO_2R^4$, $SO_3H$, cyano, —$SO_2NHR^4$ (where $R^4$ is as defined above), —$SO_2NHAr$ (where Ar is an optionally substituted phenyl or optionally substituted 5 or 6 membered heteroaryl ring), —$CONHR^5$ (where $R^5$ is H, cyano, $C_{1-4}$alkyl, OH, —$SO_2$—$C_{1-4}$alkyl, —$SO_2CF_3$, —$SO_2$-phenyl, —$(CHR^4)_r$—COOH, (where r is 1–3 and $R^4$ (as defined above) can take different values when r is 2–3)), or X is a group of formula (II)

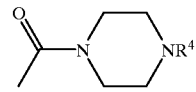

(II)

or X represents a group of formula (III)

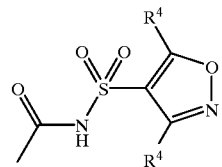

(III)

where the groups defined as $R^4$ may have different values within the definition of $R^4$ above;

A is selected from phenyl, naphthyl, furyl, pyridyl and thienyl;

$R^2$ is independently selected from trifluoromethyl, $C_{1-4}$alkyl, halo, hydroxy, $CF_3O-$, $C_{1-4}$alkoxy, $C_{1-4}$alkanoyl, $C_{1-4}$alkanoyloxy, amino, cyano, $C_{1-4}$alkylamino, $(C_{1-4}$alkyl$)_2$amino, $C_{1-4}$alkanoylamino, nitro, carboxy, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—$(C_{1-4}$alkyl)carbamoyl$C_{1-4}$alkyl, N—$(C_{1-4}$alkyl$)_2$carbamoyl-$C_{1-4}$alkyl, hydroxy$C_{1-4}$alkyl, $C_{1-4}$alkoxy$C_{1-4}$alkyl or two $R^2$ values together may form a divalent radical of the formula —$O(CH_2)_{1-4}O-$ attached to adjacent carbon atoms on ring A;

q is 0–4 and $R^2$ can have the same or different values when q is 2–4;

Z is hydrogen, fluoro, chloro, bromo, iodo, methyl, trifluoromethyl, hydroxymethyl, acetyl, carboxy$C_{3-6}$cycloalkyl or —$(CHR^4)_r$—$NR^6R^7$ (where r is 0–2, $R^6$ and $R^7$ are independently selected from H and $C_{1-4}$alkyl or $R^6$ and $R^7$ together with the nitrogen to which they are attached form a 5 or 6 membered non-aromatic ring optionally containing one further heteroatom selected from O, N or S);

or a pharmaceutically acceptable salt or an in vivo hydrolysable ester thereof.

A further aspect of the present invention provides the use of a compound of the formula (I) in the manufacture of a medicament for antagonising an MCP-1 mediated effect in a warm blooded animal, such as man wherein $R^1$ is independently selected from trifluoromethyl, $C_{1-4}$alkyl, halo, hydroxy, $C_{1-4}$alkoxy, $C_{1-4}$alkanoyl, $C_{1-4}$alkanoyloxy, amino, cyano, $C_{1-4}$alkylamino, di($C_{1-4}$alkyl)amino, $C_{1-4}$alkanoylamino, nitro, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—$(C_{1-4}$alkyl)carbamoyl$C_{1-4}$alkyl, N—$(C_{1-4}$alkyl$)_2$carbamoyl-$C_{1-4}$alkyl, hydroxy$C_{1-4}$alkyl, $C_{1-4}$alkoxy$C_{1-4}$alkyl, morpholino, pyrrolidinyl, carboxy$C_{1-4}$alkylamino, $R^3$ and —$OR^3$ (where $R^3$ is optionally substituted phenyl or an optionally substituted 5- or 6-membered heteroaryl ring);

p is 0–4 and $R^1$ can have the same or different values when p is 2–4 with the proviso that no more than one $R^1$ can be chosen from the group amino, $C_{1-4}$alkylamino, di($C_{1-4}$alkyl)amino, morpholino and pyrrolidinyl; Z is hydrogen, fluoro, chloro, bromo, iodo, methyl, trifluoromethyl, hydroxymethyl, carboxy$C_{3-6}$cycloalkyl or —$(CHR^4)_r$—$NR^6R^7$ (where r is 0–2, $R^6$ and $R^7$ are independently selected from H and $C_{1-4}$alkyl or $R^6$ and $R^7$ together with the nitrogen to which they are attached form a 5 or 6 membered non-aromatic ring optionally containing one further heteroatom selected from O, N or S); and X, T, A, $R^2$ and q have any of the values defined above; or a pharmaceutically acceptable salt or an in vivo hydrolysable ester thereof.

In this specification the term 'alkyl' includes straight chained, branched structures and ring systems. For example, "$C_{1-4}$alkyl" includes propyl, isopropyl, i-butyl and cyclopropane. However, references to individual alkyl groups such as 'propyl' are specific for the straight chained version only, references to individual branched chain alkyl groups such as 'isopropyl' are specific for the branched chain version only and references to the cyclo groups such as cyclopropane are specific to the cyclic groups only. A similar convention applies to other radicals, for example "hydroxy$C_{1-4}$alkyl" includes 1-hydroxyethyl and 2-hydroxyethyl. The term "halo" refers to fluoro, chloro, bromo and iodo.

Suitable optional substituents for aryl and heteroaryl are any of the values defined for $R^1$ and $R^2$ above. "Aryl" means phenyl or naphthyl, preferably phenyl. "Heteroaryl" means an aromatic mono- or bicyclic- 5–10 membered ring with up to three or five ring heteroatoms (in mono and bicyclic rings respectively) selected from nitrogen, oxygen and sulphur. Examples of "heteroaryl" include thienyl, pyrrolyl, furanyl, imidazolyl, thiazolyl, pyrimidinyl, pyridinyl, indolyl, benzimidazolyl, benzthiazolyl, quinolyl and isoquinolinyl.

An example of "$C_{1-4}$alkanoyloxy" is acetoxy. Examples of "$C_{1-4}$alkoxycarbonyl" include methoxycarbonyl, ethoxycarbonyl, n- and t-butoxycarbonyl. Examples of "$C_{1-4}$alkoxy" include methoxy, ethoxy and propoxy. Examples of "$C_{1-4}$alkanoylamino" include formamido, acetamido and propionylamino. Examples of "$C_{1-4}$alkylsulphanyl" include methylthio and ethylthio. Examples of "$C_{1-4}$alkylsulphinyl" include methylsulphinyl and ethylsulphinyl. Examples of "$C_{1-4}$alkylsulphonyl" include methylsulphonyl and ethylsulphonyl. Examples of "$C_{1-4}$alkanoyl" include propanoyl and ethanoyl. Examples of "$C_{1-4}$alkylamino" include methylamino and ethylamino. Examples of "di($C_{1-4}$alkyl)amino" include di-N-methylamino, di-(N-ethyl)amino and N-ethyl-N-methylamino. Examples of "$C_{1-4}$alkoxy$C_{1-4}$alkyl" methoxymethyl and propoxyethyl. Examples of "carbamoyl$C_{1-4}$alkyl" are methylcarboxamide and ethylcarboxamide. Examples of "carboxy$C_{3-6}$cycloalkyl" are 2-carboxycyclopropyl and 3-carboxycyclopentyl. Examples of "N—$(C_{1-4}$alkyl)carbamoyl$C_{1-4}$alkyl" are methylaminocarbonylethyl and ethylaminocarbonylpropyl. Examples of "N—$(C_{1-4}$alkyl$)_2$carbamoyl-$C_{1-4}$alkyl" are dimethylaminocarbonylethyl and methylethylaminocarbonylpropyl. Examples of "carboxy$C_{1-4}$alkylamino" are carboxy methyl and carboxypropyl.

A particular group of values for $R^1$ includes, for example, trifluoromethyl, (1–4C)alkyl, halogeno, hydroxy, (1–4C)alkoxy, (1–4C)alkanoyl, carboxy, trifluoromethoxy, amino, (1–4C)alkanoylamino, nitro, (1–4C)alkylsulphonyl, carboxy$C_{1-4}$alkylamino, acetyl, phenoxy, phenyl optionally bearing a dimethylamino, trifluoromethyl, fluoro, chloro, methoxy, methyl or amino group, naphthyl, thien-2-yl, 5-halogenothien-2-yl, thien-3-yl and pyridyl.

A particular value for p is 0, 1 or 2.

A particular group of values for Z includes, for example, hydrogen, fluoro, chloro, bromo, iodo, methyl, trifluoromethyl, hydroxymethyl, 2-carboxycyclopropyl, amino and acetyl.

A particular group of values for X includes, for example, carboxy, (1–4C)alkoxycarbonyl, cyano, —$CONHR^5$ wherein $R^5$ is —$SO_2CF_3$, $SO_2$—$C_{1-4}$alkyl or —$SO_2$-phenyl.

A particular group of values for $R^2$ includes, for example, trifluoromethyl, (1–4C)alkyl, halogeno, trifluoromethoxy, (1–4C)alkoxy and nitro.

Preferred values for $R^1$, p, Z, X, T, A $R^2$ and q are as follows.

Preferred values for $R^1$ are $C_{1-4}$alkoxy, halo, nitro, amino, phenoxy or trifluoromethyl, more preferably chloro and/or $C_{1-4}$alkoxy. Another preferred value for $R^1$ includes, for example, carboxymethylamino. Where $R^1$ is halo, fluoro, chloro or bromo are preferred. Where $R^1$ is $C_{1-4}$alkoxy, methoxy or ethoxy are preferred, particularly methoxy. Preferably position 7 is unsubstituted, and preferably there is no more than one $C_{1-4}$alkoxy group.

Preferably p is 1 or 2.

Preferred combinations of p and $R^1$ are as follows.

When p=1 then $R^1$ is preferably 4-methoxy, 4-phenyl, 4-amino, 5-chloro, 5-methoxy, 5-nitro, 5-bromo, 5-phenoxy, 5-fluoro, 5-amino, 6-fluoro, 6-trifluoromethyl, 6-nitro or 6-chloro more preferably 4-amino, 5-amino, 5-chloro or 6-chloro.

T is preferably —$CH_2$—.

Preferably X is carboxy or —$CONHR^5$ (where $R^5$ is defined above). Preferably $R^5$ is —$SO_2CF_3$. Most preferably X is carboxy.

Preferably A is phenyl, naphthyl, furyl and thienyl especially phenyl or thienyl. When A is thienyl it is preferably thien-2-yl. Most preferably A is phenyl.

$R^2$ is preferably chloro, bromo, methyl, methoxy, nitro, trifluoromethyl or trifluoromethoxy. Another preferred value for $R^2$ includes, for example, fluoro.

q is preferably 1 or 2, especially 2.

Preferred combinations of A, $R^2$ and q are as follows.

When A is phenyl, and q is 1, then $R^2$ is preferably chloro especially 3-chloro or 4-chloro. Another preferred value for $R^2$ includes, for example, 3-fluoro, 4-fluoro or 3-trifluoromethyl.

When A is phenyl, and q is 2, then $R^2$ is preferably chloro, especially 3,4-dichloro. Another preferred value for $R^2$ includes, for example, fluoro, especially 3,4-difluoro.

When A is phenyl then the positions ortho to T are preferably unsubstituted.

When A is thien-2-yl then preferably $R^2$ is chloro, especially 5-chloro.

Preferably Z is hydrogen, bromo or methyl, especially hydrogen.

A preferred class of compounds within formula (I) for use in the present invention is that of formula (I'):

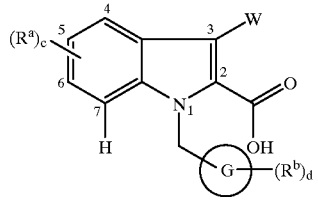

(I')

wherein:
$R^e$ is methoxy, fluoro, chloro, bromo, nitro, amino, phenoxy, trifluoromethyl, carboxy or hydroxy;
x is 1 or 2 with the proviso that there is at most one methoxy group;
X' is carboxy, —$CONHSO_2CF_3$, —CONHEt or —CONHMe;
A' is phenyl or thienyl;
$R^f$ is chloro, bromo, methyl, methoxy, nitro, trifluoromethyl or trifluoromethoxy;
y is 1 or 2;
Z' is hydrogen, methyl bromo or carboxycyclopropyl; or a pharmaceutically acceptable salt or in vivo hydrolysable ester thereof.

$R^e$ is particularly methoxy, fluoro, chloro, bromo, nitro, amino, phenoxy or trifluoromethyl.

Preferably $R^e$ is chloro, amino, fluoro, nitro or methoxy. Preferably position 7 is unsubstituted.

Preferred combinations of x and $R^e$ are as follows.

When x=1 then $R^e$ is preferably chloro, amino, fluoro, nitro or methoxy especially. 4-methoxy, 4-amino, 5-chloro, 5-methoxy, 5-nitro, 5-bromo, 5-fluoro, 5-amino, 6-fluoro, 6-nitro or 6-chloro and especially 4-methoxy or 4-amino.

When x=4 then $R^e$ is preferably F.

Z' is preferably hydrogen.

X' is preferably carboxy.

A' is preferably phenyl. Where A' is thienyl it is preferably thien-2-yl.

Preferred combinations of A', $R^f$ and y are as follows.

When A' is phenyl, and y is 1, then $R^f$ is preferably chloro especially 3-chlorophenyl or 4-chlorophenyl.

When A' is phenyl, and y is 2, then $R^f$ is preferably chloro, especially 3,4-dichlorophenyl.

When A' is phenyl then the positions ortho to the $CH_2$ moiety linked to the indole ring are preferably hydrogen.

When A' is thien-2-yl then preferably $R^f$ is chloro especially 5-chloro.

A further aspect of the present invention is a novel compound of the formula (I) or (I') as defined above.

Accordingly a further aspect of the present invention provides a novel compound of the formula (A):

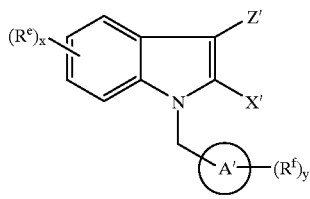

(A)

which is an inhibitor of monocyte chemoattractant protein-1 and wherein:

$R^a$ is 4-methoxy, 4-phenyl, 4-amino, 4-thien-2-yl, 5-chloro, 5-methoxy, 5-nitro, 5-bromo, 5-phenoxy, 5-fluoro, 5-carboxymethylamino, 5-amino, 6-fluoro, 6-trifluoromethyl, 6-nitro or 6-chloro;

c is 0, 1 or 2 provided that there is no more than one methoxy group;

W is hydrogen, bromo, methyl or transcyclopropyl-2-carboxylic acid;

G is phenyl or thien-2-yl;

When G is phenyl $R^b$ is 3chloro, 3-trifluoromethyl, 3-nitro, 3-methoxy, 4-trifluoromethyl, 4-trifluoromethoxy or 4-chloro;

When G is thien-2-yl $R^b$ is 5-chloro;

d is 1 or 2;

or a pharmaceutically acceptable salt or an in vivo hydrolysable ester thereof.

Preferred values for $R^a$, c, G, $R^b$, W, A and d are as follows.

Preferred values for $R^a$ are 4-methoxy, 4-amino, 5-fluoro, 5chloro, 6-chloro or 5-methoxy more preferably 4-amino or 5-fluoro.

Preferably c is 0 or 1 more preferably 1.

Preferred combinations of c and Ra are as follows.

When c=1 then $R^a$ is preferably 4-amino, 4-thien-2-yl, 4-methoxy, 5-chloro, 5-fluoro, 5-amino, 6-fluoro or 6-chloro, but 4-amino, 4-thien-2-yl and 5-fluoro are most preferred.

W is preferably bromo or hydrogen, especially hydrogen.

Preferably G is phenyl.

Preferably d is 2.

When G is phenyl preferably $R^b$ is 3-chloro, 3-trifluoromethyl or 4-chloro.

Preferred combinations of G, d and $R^b$ are as follows.

When G is phenyl and d is 1, then G taken together with $R^b$ is preferably 3-chlorophenyl, 4-chlorophenyl, 3-iodophenyl, 4-iodophenyl or 3-trifluoromethylphenyl, and especially 3-chlorophenyl, 4-chlorophenyl or 3-trifluoromethylphenyl.

When G is phenyl and d is 2 then G taken together with $R^b$ is preferably 3,4-dichlorophenyl or 3,4-difluorophenyl, especially 3,4-dichlorophenyl.

A further aspect of the present invention provides a novel compound of the formula (B)

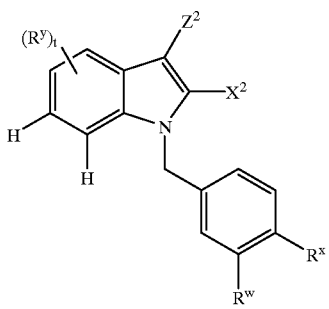

(B)

wherein $X^2$ is carboxy, —$CONHSO_2CH_3$ or —$CONHSO_2$-phenyl; $Z^2$ has any of the meanings, including particular and preferred values, for Z or Z' defined herein; $R^w$ and $R^x$ are independently halogeno; $R^y$ is independently selected from any of the meanings, including particular and preferred values, for $R^1$ or $R^e$ defined herein; and t is 1 or 2; or a pharmaceutically acceptable salt thereof. Within this group of compounds, those in which $R^w$ and $R^x$ are both fluoro or both chloro are particularly preferred, and especially those in which $R^w$ and $R^x$ are both chloro. Compounds in which $X^2$ is carboxy are also particularly preferred.

Compounds of formulas (I), (I'), (A) and/or (B) which are of particular interest include, for example, the specific embodiments set out hereinafter in the accompanying examples, especially Examples 3 and 3.01 to 3.111 inclusive, and these compounds and/or the use of these compounds are provided as a further feature of the invention. Of these, preferred compounds include the compounds described in Examples 3, 3.01, 3.02, 3.03, 3.04, 3.08, 3.10, 3.11, 3.12, 3.13, 3.14, 3.16, 3.17, 3.18, 3.19, 3.20, 3.21, 3.22, 3.24, 3.25, 3.27, 3.28, 3.29, 3.30, 3.32, 3.33, 3.34, 3.35, 3.43, 3.44, 3.45, 3.46, 3.47, 3.48, 3.49, 3.50, 3.51, 3.52, 3.54, 3.55, 3.57, 3.58, 3.59, 3.60, 3.61, 3.62, 3.63, 3.64, 3.65, 3.66, 3.67, 3.68, 3.69, 3.70, 3.71, 3.72, 3.73, 3.75, 3.76, 3.77, 3.78, 3.79, 3.80, 3.81, 3.82, 3.83, 3.85, 3.86, 3.87, 3.88, 3.89, 3.90, 3.91, 3.92, 3.93, 3.94, 3.95, 3.97, 3.98, 3.99, 3.100, 3.101, 3.102, 3.103, 3.104, 3.105, 3.106, 3.107, 3.108, 3.109, 3.110 and 3.111, or a pharmaceutically acceptable salt or an in vivo hydrolysable ester thereof. Of these, paticularly preferred compounds include the compounds described in Examples 3.02, 3.03, 3.11, 3.12, 3.14, 3.22, 3.30, 3.46, 3.54, 3.58, 3.59, 3.60, 3.61, 3.68, 3.69, 3.73, 3.82, 3.83, 3.86, 3.88, 3.90, 3.92, 3.93, 3.94, 3.100, 3.105, 3.106, 3.107, 3.108, 3.109 and 3.111, or a pharmaceutically acceptable salt or an in vivo hydrolysable ester thereof.

Suitable pharmaceutically acceptable salts include acid addition salts such as methanesulfonate, fumarate, hydrochloride, hydrobromide, citrate, maleate and salts formed with phosphoric and sulphuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically acceptable salt is a sodium salt.

Some compounds of formula (I) may possess chiral centres. It is to be understood that the invention encompasses all such optical isomers and diasteroisomers of compounds of formula (I).

The invention further relates to all tautomeric forms of the compounds of formula (A), (B) or formula (I).

It is also to be understood that certain compounds of formula (A), formula (B) or formula (I) can exist in solvated as well as unsolvated forms such as, for example, hydrated forms. It is to be understood that the invention encompasses all such solvated forms.

An in vivo hydrolysable ester of a compound of formula (A) or formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of formula (A) or formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Another aspect of the present invention provides a process for preparing a compound of formula (A) or a pharmaceutically acceptable salt or an in vivo hydrolysable ester thereof which process comprises of:

a) reacting compounds of formula (IV):

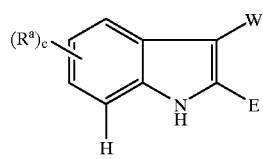

(IV)

where E is carboxy protected in the form of an ester and other groups are as defined in formula (A) with a compound of formula (V):

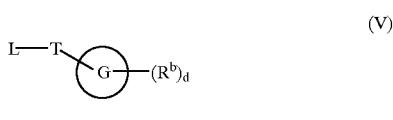

where L is a leaving group and other groups are as defined in formula (A) to give a compound of formula (VI):

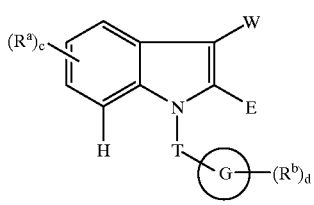

where E is carboxy protected as an ester.

b) optionally interconverting a compound of formula (VI) to give another compound of formula (VI), wherein any functional groups are protected if necessary and optionally:

i) removing any protecting groups;

ii) optionally forming a pharmaceutically acceptable salt or in vivo hydrolysable ester.

Compounds of formula (VI) may be interconverted for example as described herein or by known processes such as functional group modification or aromatic substitution.

Preferred values for L are chloro and bromo. Preferred values for E are —$CO_2Et$ and —$CO_2Me$.

Compounds of formula (IV) and (V) may be reacted together in an inert solvent and a base such as N,N-dimethylformamide/sodium hydride or dichloromethane/sodium hydroxide (optionally in the presence of a phase transfer catalyst such as tetra-n-butylammonium hydrogensulphate) for 1–6 hours preferably 1–3 hours, at a temperature of 15–30° C., preferably 20–25° C. to give a compound of formula (VI).

Compounds of formula (IV) are commercially available, made by modification using known processes of commercially available compounds of formula (IV), or they are prepared by:

a) Reacting a compound of formula (VII):

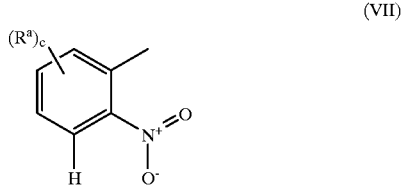

where $R^1$ and p are as defined in formula (A), with a compound of formula (VIII)

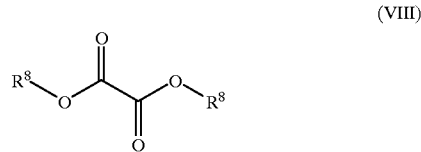

where $R^8$ is $C_{1-4}$alkyl.

Compounds of formula (VII) and (VIII) are reacted together under Reissert reaction conditions such as in an inert solvent (such as tetrahydrofuran), in the presence of a base (such as potassium ethoxide), at a temperature range of 15–30° C. preferably 20–25° C., for 10–20 hours preferably 15–17 hours. The resulting compound is isolated and dissolved in an alcohol such as ethanol and an organic acid (such as acetic acid) and a transition metal catalyst (such as 10% Pd/C) and cyclohexene is added. The mixture is heated at a temperature of 60–120° C. preferably at 70–90° C. for 15–25 hours preferably 16–20 hours to give a compound of formula (IV); or b) Reacting a compound of formula (IX):

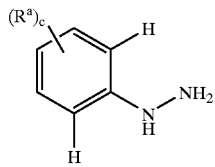

where $R^1$ and p are as defined for formula (A), with a compound of formula (X):

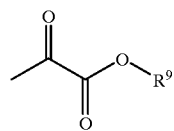

where $R^9$ is $C_{1-4}$alkyl.

Compounds of formula (IX) and (X) are reacted together under Fischer conditions such as with an organic acid (such as acetic acid), in an alcohol (such as ethanol), at a temperature of 60–90° C., preferably 75–85° C., for 1–5 hours, preferably 1–3 hours. The resulting compound is mixed with a strong acid (such as polyphosphoric acid) and heated at 90–150° C. preferably 100–120° C., for 0.5–4 hours, preferably 0.5–2 hours to give a compound of formula (IV) in which W is hydrogen. Then, if desired, W can be optionally converted into another value of W as defined in formula (A) using techniques known in the art such as those described below.

Compounds of formula (V), (VII), (VIII), (IX) and (X) are known or commercially available or are prepared by processes known in the art by standard manipulation of commercially available or known materials.

$R^8$ and $R^9$ are $C_{1-4}$alkyl. Preferably $R^8$ and $R^9$ are methyl or ethyl.

It will be appreciated that analogous procedures to those described above may be used to prepare compounds of the formula (I), (I') and (B).

It will also be appreciated that certain of the various optional substituents in the compounds of formula (A), (B), (I) and (I') may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with beating; oxidation of alkylthio to alkylsulphinyl or alkylsulphonyl. Specific examples of the substitution and modification reactions prior to or immediately following the processes mentioned above are illustrated, but not limited by, the following examples in which variable groups are as defined for formula (A) unless otherwise stated.

1) Modification of $R^a$.
   a) For $R^a$=Ar (phenyl or thienyl): compounds of formula (XI)

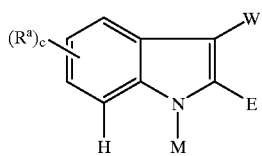

where E is carboxy protected as an ester and M is H, a nitrogen protecting group or the group

and $R^a$ is Br are coupled with compounds of formula (XII)

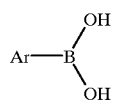

to give compounds of formula (XI) where $R^a$=Ar. It will be appreciated that an analogous procedure may be used to prepare compounds of formula (I) in which $R^1$ is optionally substituted phenyl or optionally substituted 5 or 6 membered heteroaryl ring. Suitable reaction conditions are set out below.

Compounds of formula (XI) where $R^a$=Br and (XII) are reacted together in the presence of a transition metal catalyst (for example tetrakis(triphenylphosphine)palladium(0)), in an inert solvent (such as toluene) and an alcohol (such as ethanol), with an aqueous base (such as potassium carbonate), preferably in an inert atmosphere, at a temperature of 60–100° C. preferably 75–85° C. for 14–20 hours preferably 15–17 hours.

b) For $R^a$=NH$_2$; compounds of formula (XI) where $R^a$=NO$_2$ are reduced under standard conditions to give a compound of formula (XI) where $R^a$=NH$_2$. Suitable reaction conditions are set out below.

Compounds of formula (XI) where $R^a$=NO$_2$ are reacted with a reducing agent (such as sodium borohydride) and stannous chloride dihydrate in an alcohol (such as ethanol) at a temperature of 30–80° C. preferably 50–70° C. for 2–10 hours preferably 4–6 hours.

2) Hydrolysing a compound of formula (VI) as defined above to give a compound of formula (XIII):

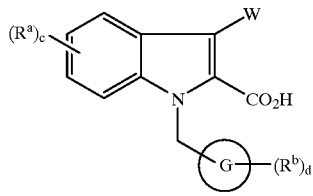

Suitable reaction conditions are set out below.
   i) The general case where $X^a$ is carboxy protected as an ester—in an inert solvent (such as tetrahydrofuran) and an alcohol (such as methanol), in the presence of a base (for example sodium hydroxide), at a temperature range of 10–50° C. preferably 20–30° C. for 1–25 hours preferably 15–20 hours followed by the addition of water and an acid (such as acetic acid).
   ii) Specifically where $X^a$ is —CO$_2$Me— with a salt (such as lithium iodide), in an organic base (such as pyridine), at a temperature range of 100–125° C. especially 115–120° C. for 3–10 hours preferably 5–7 hours followed by the addition of aqueous acid (for example 2M hydrochloric acid).

3) Modification of W.
   a) For W=Br: compounds of formula (XI) where W=hydrogen may be brominated under standard conditions to give a compound of formula (XI) where W=Br. Suitable reaction conditions are set out below.

Compounds of formula (XI) where W=bromine may be prepared by reacting a compound of formula (XI) where W=hydrogen in an inert solvent (such as N,N-dimethylformamide) with bromine for 5–55 minutes particularly 25–35 minutes at 10–30° C., preferably 20–25 ° C.

The reader is also directed to patent nos. US 005,389,650A, US 005,290,798A, EP 0535926A1, EP 0535923A1, US 005,190,968A, EP 0535924A1, EP 0419049A1, U.S. Pat. No. 5,308,850, EP 0535925A1, WO 93/16069, WO 93/25546, US 005,273,980A and U.S. Pat. No. 5,272,145, WO 93/20078, EP 0186367, EP 0275667, US 4,965,369A (process patent) WO 94/14434, EP 0480659 A2 and WO 96/03377A for synthetic details of benzyl indole compounds.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

When a pharmaceutically-acceptable salt of a compound of formula (A), formula (B) or formula (I) is required, it may be obtained, for example, by reaction of said compound with the appropriate acid (which affords a physiologically acceptable anion), or with the appropriate base (which affords a physiologically acceptable cation), or by any other conventional salt formation procedure.

When an optically active form of a compound of formula (I) is required, it may be obtained, for example, by carrying out one of the aforesaid procedures using an optically active starting material or by resolution of a racemic form of said compound using a conventional procedure.

According to a further aspect of the present invention there is provided a method for antagonising an MCP-1 mediated effect in a warm blooded animal, such as man, in need of such treatment, which comprises administering to said animal an effective amount of a compound of formula (A), formula (B) or formula (I), or a pharmaceutically acceptable salt, or an in vivo hydrolysable ester thereof.

According to a further feature of the invention there is provided a method of treatment of diseases or medical conditions mediated by MCP-1 which comprises administering to a warm-blooded animal an effective amount of a compound of formula (A), formula (B) or formula (I), or a pharmaceutically acceptable salt, or an in vivo hydrolysable ester thereof. According to a further aspect of the invention there is provided the use of a compound of the formula (I), (A) or (B) in the manufacture of a medicament for use in the treatment of a disease or medical condition mediated by MCP-1. Such diseases may include, for example, any of those previously referred to herein. According to a further aspect of the invention there is provided a compound of the formula (A) or (B), or a pharmaceutically acceptable salt thereof or an in vivo hydrolysable ester thereof, for use in a method of treatment of the human or animal body by therapy. According to a further aspect of the invention there is provided a method of inhibiting the binding of MCP-1 to a receptor thereof in a warm-blooded animal in need thereof which comprises administering to said warm-blooded animal an effective amount of a compound of formula (A), formula (B) or formula (I), or a pharmaceutically acceptable salt, or an in vivo hydrolysable ester thereof. According to a further aspect of the invention there is provided the use of a compound of the formula (I), (A) or (B) in the manufacture of a medicament for use in inhibiting the binding of MCP-1 to a receptor thereof.

In order to use a compound of formula (A), formula (B) or formula (I) or a pharmaceutically acceptable salt or an in vivo hydrolysable ester thereof for the therapeutic treatment of mammals including humans, especially in treating inflammation, it is normally formulated in accordance with standard pharmaceutical practice as a pharmaceutical composition.

Therefore in another aspect the present invention provides a pharmaceutical composition which comprises a compound of formula (A) or a pharmaceutically acceptable salt or an in vivo hydrolysable ester thereof and a pharmaceutically acceptable diluent or carrier. In another aspect the present invention provides a pharmaceutical composition which comprises a compound of formula (B) or a pharmaceutically acceptable salt thereof and a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for-oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insulation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The following illustrate, but are not intended to limit, representative pharmaceutical dosage forms of the invention as defined herein (the active ingredient being termed "Compound X"), for therapeutic or prophylactic use in humans:

| (a) Tablet I | mg/tablet |
|---|---|
| Compound X. | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1 M Sodium hydroxide solution | 15.0% w/v |
| 0.1 M Hydrochloric acid | to adjust PH to 7.6 |
| Polyethylene glycol 490 | 4.5% w/v |
| Water for injection | to 100% |

| (f) Injection II | (10 mg/ml) |
|---|---|
| Compound X | 1.0% w/v |
| Sodium phosphate BP | 3.6% w/v |
| 0.1 M Sodium hydroxide solution | 15.0% w/v |
| Water for injection | to 100% |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μg |
| Water | 300 μl |
| 1-Dodecylazacycloheptan-2-one | 50 μl |
| Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

Biological Testing

The following biological test methods, data and Examples serve to illustrate the present invention.

Abbreviations:

| ATCC | American Type Culture Collection, Rockville, U.S.A. |
|---|---|
| BCA | bicinchroninic acid, (used, with copper sulphate, to assay protein) |
| DMEM | Dulbecco's modified Eagle's medium |
| EGTA | ethylenebis(oxyethylenenitrilo)tetraacetic acid |
| FCS | foetal calf serum |
| HBSS | Hank's Balanced Salt Solution |
| hMCP-1 | human Monocyte Chemoattractant Protein-1 |
| PBS | phosphate buffered saline |
| PCR | polymerase chain reaction |

AMPLITAQ™, available from Perkin-Elmer Cetus, is used as the source of thermostable DNA polymerase.

Binding Buffer is 50 mM HEPES, 1 mM $CaCl_2$, 5 mM $MgCl_2$, 0.5% foetal calf serum, adjusted to pH 7.2 with 1 M NaOH.

Non-Essential Amino Acids (100×concentrate) is: L-Alanine, 890 mg/l; L-Asparagine, 1320 mg/l; L-Aspartic acid, 1330 mg/l; L-Glutamic acid, 1470 mg/l; Glycine, 750 mg/l; L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt); 5000 units/ml; Streptomycin sulphate, 5000 µg/ml.

Human monocytic cell line THP-1 cells are available from ATCC, accession number ATCC TIB-202.

Hank's Balanced Salt Solution (HBSS) was obtained from Gibco; see *Proc. Soc. Exp. Biol. Med.*, 1949, 71, 196.

Synthetic cell culture medium, RPMI 1640 was obtained from Gibco; it contains inorganic salts [$Ca(NO_3)_2 \cdot 4H_2O$ 100 mg/l; KCl 400 mg/l; $MgSO_4 \cdot 7H_2O$ 100 mg/l; NaCl 6000 mg/l; $NaHCO_3$ 2000 mg/l & $Na_2HPO_4$ (anhyd) 800 mg/l], D-Glucose 2000 mg/l, reduced glutathione 1 mg/l, amino acids and vitamins.

FURA-2/AM is
1-[2-(5-carboxyoxazol-2-yl)-6-aminobenzofuran-5-oxy]-2-(2'-amino-5'-methylphenoxy)-ethane-N,N,N',N'-tetraacetic acid pentaacetoxymethyl ester and was obtained from Molecular Probes, Eugene, Oreg., USA.

General molecular biology procedures can be followed from any of the methods described in "Molecular Cloning—A Laboratory Manual" Second Edition, Sambrook, Fritsch and Maniatis (Cold Spring Harbor Laboratory, 1989).

Biological Assays for hMCP-1 Antagonists a) hMCP-1 Receptor-binding assay i) Cloning and expression of hMCP-1 receptor The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci.* USA, 91, 2752). The resulting PCR products were cloned into vector PCR-II™ (InVitrogen, San Diego, Calif.). Error free CCR2B cDNA was subcloned as a Hind III-Not I fragment into the eukaryotic expression vector pCDNA3 (InVitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell*, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.*, 6, 134). CHO-K1 clone 7 (CHO-CCR2B) was identified as the highest MCP-1 receptor B expressor.

ii) Preparation of membrane fragments

CHO-CCR2B cells were grown in DMEM supplemented with 10% foetal calf serum, 2 mM glutamine, 1× Non-Essential Amino Acids, 1× Hypoxanthine and Thymidine Supplement and Penicillin-Streptomycin (at 50 µg streptomycin/ml, Gibco BRL). Membrane fragments were prepared using cell lysis/differential centrifugation methods as described previously (Siciliano et al., 1990, *J. Biol. Chem.*, 265, 19658). Protein concentration was estimated by BCA protein assay (Pierce, Rockford, Ill.) according to the manufacturer's instructions.

iii) Assay $^{125}$I MCP-1 was prepared using Bolton and Hunter conjugation (Bolton et al., 1973, *Biochem. J.*, 133, 529; Amersham International plc]. Equilibrium binding assays were carried out using the method of Ernst et al., 1994, *J. Immunol.*, 152, 3541. Briefly, varying amounts of $^{125}$I-labeled MCP-1 were added to 10 mg of purified CHO-CCR2B cell membranes in 100 ml of Binding Buffer. After 1 hour incubation at room temperature the binding reaction mixtures were filtered and washed 5 times through a plate washer (Packard Harvester Filtermate™ 196). Scintillation fluid (25 µl, Microscint™-20, a high efficiency liquid scintillation counting cocktail for aqueous samples) was added to each well and the plate was covered with plate sealer and counted (Packard Top Count™). Cold competition studies were performed as above using 100 pM $^{125}$I-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B was present at a concentration of 0.2 pmoles/mg of membrane protein and bound MCP-1 selectively and with high affinity ($IC_{50}$=110 pM, $K_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Test compounds dissolved in DMSO (5 µl) were tested in competition with 100 pM labelled MCP-1 over a concentration range (0.1–200 µM) in duplicate using eight point dose-response curves and $IC_{50}$ concentrations were calculated.

b) MCP-1 mediated calcium flux in THP-1 cells

The human monocytic cell line THP-1 was grown in a synthetic cell culture medium RPMI 1640 supplemented with 10% foetal calf serum, 2 mM glutamine and Penicillin-Streptomycin (at 50 µg streptomycin/ml, Gibco BRL). THP-1 cells were washed in HBSS (lacking $Ca^{2+}$ and $Mg^{2+}$)+1 mg/ml BSA and resuspended in the same buffer at a density of $3 \times 10^6$ cells/ml. The cells were then loaded with 1 mM FURA-2/AM for 30 min at 37° C., washed twice in HBSS, and resuspended at $1 \times 10^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA, 1 mM $MgCl_2$ and 2 mM $CaCl_2$. The cuvette was placed in a fluorescence spectrophotometer (Perkin Elmer, Norwalk, Conn.) and pre-incubated for 4 min at 37° C. with stirring. Fluorescence was recorded over 70 sec and cells were stimulated by addition of hMCP-1 to the cuvette after 10 sec. [$Ca^{2+}$]i was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic [$Ca^{2+}$] according to the equation:

$$[Ca^{2+}]i = K_d \frac{(R - R\min)}{(R\max - R)}(Sf2/Sb2)$$

where the $K_d$ for FURA-2 $Ca^{2+}$ complex at 37° C. was taken to be 224 nm. $R_{max}$ is the maximal fluorescence ratio determined after addition of 10 mM Ionomycin, $R_{min}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with HMCP-1 induced a rapid, transient rise in [$Ca^{2+}$]i in a specific and dose dependent manner. Dose response curves indicated an approximate $EC_{50}$ of 2 nm. Test compounds dissolved in DMSO (10 µl)

were assayed for inhibition of calcium release by adding them to the cell suspension 10 sec prior to ligand addition and measuring the reduction in the transient rise in [$Ca^{2+}$]. Test compounds were also checked for lack of agonism by addition in place of hMCP-1.

c) hMCP-1 mediated chemotaxis assay

In vitro chemotaxis assays were performed using either the human monocytic cell line THP-1 or peripheral blood mixed monocytes obtained from fresh human blood purified by erythrocyte sedimentation followed by density gradient centrifugation over 9.6% (w/v) sodium metrizoate and 5.6% (w/v) polysaccharide, density 1.077 g/ml (Lymphopre™ Nycomed). Cell migration through polycarbonate membranes was measured by enumerating those passing through either directly by Coulter counting or indirectly by use of a colourimetric viability assay measuring the cleavage of a tetrazolium salt by the mitochondrial respiratory chain (Scudiero D. A. et al. 1988, *Cancer Res.*, 48, 4827–4833).

Chemoattractants were introduced into a 96-well microtiter plate which forms the lower well of a chemotaxis chamber fitted with a PVP-free 5 μm poresize polycarbonate adhesive framed filter membrane (NeuroProbe MB series, Cabin John, Md. 20818, USA) according to the manufacturer's instructions. The chemoattractant was diluted as appropriate in synthetic cell culture medium, RPMI 1640 (Gibco) supplemented with 2 mM glutamine and 0.5% BSA. Each dilution was degassed under vacuum for 30 min and was placed (400 μl) in the lower wells of the chamber and THP-1 cells ($5\times10^5$ in 100 μl RPMI 1640+0.5% BSA) were incubated in each well of the upper chamber. For the inhibition of chemotaxis the chemoattractant was kept at a constant submaximal concentration determined previously for each chemokine and added to the lower well together with the test compounds dissolved in DMSO (final DMSO concentration <0.05% v/v) at varying concentrations. The chamber was incubated for 2 h at 37° C. under 5% $CO_2$. The medium was removed from the upper wells which were then washed out with 200 μl physiological saline before opening the chamber, wiping dry the membrane surface and centrifuging the 96-well plate at 600 g for 5 min to harvest the cells. Supernatant (150 μl) was aspirated and 10 μl of cell proliferation reagent, WST-1, {4-[3-(4-iodophenyl)-2-(4-nitrophenyl)-2H-5-tetrazolio]-1,3-benzene disulfonate} plus an electron coupling reagent (Boehringer Mannheim, Cat.no. 1644 807) was added back to the wells. The plate was incubated at 37° C. for 3 h and the absorbance of the soluble formazan product was read on a microtitre plate reader at 450 nm. The data was input into a spreadsheet, corrected for any random migration in the absence of chemoattractant and the average absorbance values, standard error of the mean, and significance tests were calculated. hMCP-1 induced concentration dependent cell migration with a characteristic biphasic response, maximal 0.5–1.0 nm.

Compounds tested of the present invention generally had $IC_{50}$ values of less than 50 μM in the hMCP-1 receptor binding assay described herein. For example the compound of example 3.23 had an $IC_{50}$ of 7.38 μM.

The invention is further illustrated, but not limited by the following Examples.

GENERAL PROCEDURES

N,N-Dimethylformamide (DMF) was dried over 4 Å molecular sieves. Anhydrous tetrahydrofuran (THF) was obtained from Aldrich SURESEAL™ bottles. Other comunercially available reagents and solvents were used without further purification unless otherwise stated. Organic solvent extracts were dried over anhydrous $MgSO_4$. $^1H$, $^{13}C$ and $^{19}F$ NMR were recorded on Bruker WM200, WM250, WM300 or WM400 instruments using $Me_2SO$-$\delta_6$ with $Me_4Si$ or $CCl_3F$ as internal standard as appropriate, unless otherwise stated. Chemical shifts are in δ (ppm) and peak multiplicities are designated as follows: s, singlet; d, doublet; dd, doublet of doublets; t, triplet; dt, doublet of triplets; q, quartet; m, multiplet; br, broad. Mass spectra were recorded on VG 12-12 quadrupole, VG 70-250 SE, VG ZAB 2-SE or a VG modified AEI/Kratos MS9 spectrometers. For TLC analysis, Merck precoated TLC plates (silica gel 60 F254, d=0.25 mm) were used. Flash chromatography was performed on silica (Merck Kieselgel: Art.9385). Melting point determinations were performed on a Kofler block or with a Büchi melting point apparatus and are uncorrected. All temperatures are in degrees Centigrade. In Example 3.11 and the following examples where the yield is quoted as, for example, "52% yield (2 steps)", this means that the % yield given is the overall yield for the two steps of alkylation of the appropriate indole followed by ester hydrolysis.

EXAMPLE 1

Ethyl N-(4-chlorobenzyl)indole-2-carboxylate

Ethyl indole-2-carboxylate (0.5 g) was dissolved in DMF and sodium hydride (0.116 g) was added in a single portion. The reaction was stirred for 1 hour, then 4-chlorobenzyl chloride (0.468 g) was added dropwise. Stirring was continued for a further 2 hours and then the reaction was quenched by the addition of water. The reaction mixture was partitioned between water and ethyl acetate. Combined organic extracts were dried ($MgSO_4$) and concentrated in vacuo and the residue purified by column chromatography using isohexane-5% ethyl acetate as eluent to give the desired end product as a white solid (0.61 g, 74%), mp 107–108°; NMR δ($CD_3SOCD_3$) 1.25 (t, 3H), 4.3 (q, 2H), 5.8 (s, 2H), 7.1 (t, 1H), 7.3 (m, 4H), 7.55 (d, 1H), 7.7 (d, 1H); M/z (+) 314 ($MH^+$).

EXAMPLES 1.01–1.09

The procedure described in Example 1 was repeated using the appropriate indole-2-carboxylic ester and benzyl halide. Thus there were obtained the compounds described below.

EXAMPLE 1.01

Ethyl N-(3-chlorobenzyl)indole-2-carboxylate in 58% yield; M/z (+) 314 ($MH^+$).

EXAMPLE 1.02

Ethyl N-(3,4-dichlorobenzyl)indole-2-carboxylate in 60% yield; M/z (+) 349 ($MH^+$).

EXAMPLE 1.03

Ethyl N-(3,4-dichlorobenzyl)-5-nitroindole-2-carboxylate in 93% yield, mp 133–4°; NMR δ($CD_3SOCD_3$) 1.26 (t, 3H), 4.24 (q, 2H), 5.86 (s, 2H), 6.80–8.80 (m, 7H); M/z (–) 393 ($M^+$), 391, 250, 136, 113.

EXAMPLE 1.04

Ethyl 5-bromo-N-(3,4-dichlorobenzyl)indole-2-carboxylate in 85% yield, mp 95–96°; NMR δ($CD_3SOCD_3$) 1.24 (t, 3H), 4.28 (q, 2H), 5.82 (s, 2H), 6.84 (d, 1H), 7.30–7.63 (m, 5H), 7.98 (s, 1H).

EXAMPLE 1.05

Ethyl N-(3,4-dichlorobenzyl)-5-phenylindole-2-carboxylate in 36% yield; NMR δ($CD_3SOCD_3$) 1.23 (t, 3H), 4.28 (q, 2H), 5.82 (s, 2H), 6.90 (d, 1H), 7.24–7.68 (m, 11H), 7.96 (s, 1H); M/z (+) 423 (M$^+$), 350, 220, 159.

EXAMPLE 1.06

Ethyl N-(3,4-dichlorobenzyl)-5-(N-morpholino)-indole-2-carboxylate in 57% yield; NMR δ(CD$_3$SOCD$_3$) 1.24 (t, 3H), 3.03 (t, 4H), 3.73 (t, 4H), 4.25 (q, 2H), 5.76 (s, 2H), 6.87 (d, 1H), 7.05–7.30 (m, 4H), 7.48 (t, 2H); M/z (+) 433 (M$^+$), 364.

EXAMPLE 1.07

Ethyl N-(3,4-dichlorobenzyl)-5-(N-pyrrolidino)-indole-2-carboxylate in 100% yield; M/z (+) 417 (M$^+$).

EXAMPLE 1.08

Ethyl N-(3,4-dichlorobenzyl)-5-phenoxyindole-2-carboxylate in 75% yield; M/z (+) 440 (M$^+$).

EXAMPLE 1.09

Ethyl N-(3,4-dichlorobenzyl)-5-methoxy-3-(trans-2-methoxycarbonylcyclopropan-1-yl)indole-2-carboxylate in 85% yield; NMR δ(CDCl$_3$) 1.34 (t, 3H), 1.47 (m, 1H), 1.75 (m, 1H), 2.02 (m, 1H), 2.83 (m, 1H), 3.80 (s, 3H), 3.88 (s, 3H), 4.22–4.48 (m, 2H), 5.63 (s, 2H), 6.80–7.35 (m, 6H); M/z (+) 476 (M$^+$), 444, 430, 163, 123, 102.

EXAMPLE 1.10

Methyl 3-bromo-5-chloro-N-(3,4-dichlorobenzyl)indole-2-carboxylate in 43% yield; NMR δ(CD$_3$SOCD$_3$) 3.85 (s, 3H), 5.8 (s, 2H), 6.88 (d, 1H), 7.37 (d, 1H), 7.43 (dd, 1H), 7.52 (d, 1H), 7.615 (d, 1H), 7.72 (d, 1H).

EXAMPLE 1.11

Ethyl 3-acetyl-N-(3,4-dichlorobenzyl)indole-2-carboxylate in 47% yield; NMR δ(CD$_3$SOCD$_3$) 1.25 (t, 3H), 2.6 (s, 3H), 4.4 (q, 2H), 5.6 (s, 2H), 7.4 (m, 5H), 8.0 (d, 1H); M/z (+) 390 (M$^+$).

EXAMPLE 1.12

Ethyl 5-acetyl-N-(3,4-dichlorobenzyl)indole-2-carboxylate in 78% yield; NMR δ(CD$_3$SOCD$_3$) 1.25 (t, 3H), 2.6 (s, 3H), 4.3 (q, 2H), 5.85 (s, 2H), 6.9 (m, 1H), 7.3 (m, 1H), 7.5 (m, 2H), 7.7 (d, 1H), 7.9 (m, 1H), 8.45 (m, 1H); M/z (+) 390 (M$^+$).

EXAMPLE 1.13

Isopropyl N-(3,4-dichlorobenzyl)-3-methylindole-2-carboxylate in 79% yield; NMR δ(CD$_3$SOCD$_3$) 1.25 (d, 6H), 2.55 (s, 3H), 5.1 (m, 1H), 5.7 (s, 2H), 6.85 (m, 1H), 7.1 (m, 1H), 7.3 (m, 2H), 7.5 (m, 2H), 7.7 (d, 1H); M/z (+) 376 (M$^+$).

EXAMPLE 2

Ethyl 3-bromo-N-(3,4-dichlorobenzyl)indole-2-carboxylate

Powdered sodium hydroxide (0.5 g) was added in a single portion to a vigorously stirred solution of ethyl 3-bromoindole-2-carboxylate (0.3 g), 3,4-dichlorobenzyl bromide (0.32 g) and tetra-n-butylammonium hydrogensulphate (50 mg) in dichloromethane. The reaction was stirred for 3 hours then partitioned between 2M HCl and ethyl acetate. Combined organic extracts were dried (MgSO$_4$) and concentrated in vacuo and the residue purified by column chromatography using isohexane-5% ethyl acetate as eluent to give the desired end product as a colourless oil (0.35 g, 73%); NMR δ(CDCl$_3$) 1.42 (t, 3H), 4.41 (q, 2H), 5.73 (s, 2H), 6.84 (d, 1H), 7.18–7.40 (m, 5H), 7.74 (d, 1H); M/z (+) 428 (MH$^+$), 426, 346, 159.

EXAMPLES 2.01–2.02

The procedure described in Example 2 was repeated using the appropriate indole-2-carboxylic ester and benzyl halide. Thus there were obtained the compounds described below.

EXAMPLE 2.01

Ethyl N-(3,4-dichlorobenzyl)-6-nitroindole-2-carboxylate in 67% yield; NMR δ(CDCl$_3$) 1.40 (t, 3H), 4.38 (q, 2H), 5.83 (s, 2H), 6.88 (m , 1H), 7.13 (m, 1H), 7.37 (d, 1H), 7.43 (s, 1H), 7.80 (d, 1H), 8.04 (dd, 1H), 8.32 (s, 1H); M/z (+) 393 (M$^+$), 339, 246, 171, 138.

EXAMPLE 2.02

Ethyl N-(3,4-dichlorobenzyl)-4-nitroindole-2-carboxylate in 69% yield; NMR δ(CDCl$_3$) 1.44(t, 3H), 4.42 (q, 2H), 5.84 (s, 2H), 6.84 (m ,1H), 7.12–7.68 (m, 4H), 8.07 (s, 1H), 8.22 (d, 1H); M/z (+) 393 (M$^+$), 339, 246, 171, 138.

EXAMPLE 2.03

Ethyl N-(3,4-dichlorobenzyl)-5,7-difluoroindole-2-carboxylate in 83% yield; NMR δ(CDCl$_3$) 1.4 (t, 3H), 4.4 (q, 2H), 5.9 (s, 2H), 6.8–6.9 (m, 2H), 7.1–7.4 (m, 4H); M/z (+) 386 (MH$^+$), 385, 384, 383.

EXAMPLE 2.04

Ethyl N-(3,4-dichlorobenzyl)-4-trifluoromethylindole-2-carboxylate in 71% yield; M/z (+) 416 (MH$^+$).

EXAMPLE 2.05

Ethyl N-(3,4-dichlorobenzyl)-5-trifluoromethylindole-2-carboxylate in 71% yield; M/z (+) 416 (MH$^+$).

EXAMPLE 2.06

Ethyl N-(3,4-dichlorobenzyl)-7-trifluoromethylindole-2-carboxylate in 53% yield; M/z (+) 416 (MH$^+$).

EXAMPLE 2.07

Ethyl 4-chloro-N-(3,4-dichlorobenzyl)indole-2-carboxylate in 87% yield; M/z (+) 382 (M$^+$).

EXAMPLE 2.08

Ethyl 4,5-dichloro-N-(3,4-dichlorobenzyl)indole-2-carboxylate in 67% yield; M/z (+) 417 (M$^+$).

EXAMPLE 2.09

Ethyl N-(3,4-dichlorobenzyl)-4-fluoroindole-2-carboxylate in 86% yield; M/z (+) 366 (M$^+$).

EXAMPLE 2.10

Ethyl N-(3,4-dichlorobenzyl)-6-fluoroindole-2-carboxylate in 71% yield; M/z (+) 366 (M$^+$).

EXAMPLE 2.11

Ethyl N-(3,4-dichlorobenzyl)-7-fluoroindole-2-carboxylate in 71% yield; M/z (+) 366 (M$^+$).

EXAMPLE 2.12

Ethyl 7-bromo-N-(3,4-dichlorobenzyl)indole-2-carboxylate in 74% yield; M/z (+) 427 (M+).

EXAMPLE 2.13

Methyl 3-amino-N-(3,4-dichlorobenzyl)indole-2-carboxylate in 64% yield; NMR δ($CD_3SOCD_3$) 3.8 (s, 3H), 5.6 (s, 2H), 6.0 (s, 2H), 6.8–7.0 (m, 2H), 7.2–7.5 (m, 4H), 7.8 (d, 1H); M/z (+) 349 (M+).

EXAMPLE 2.14

Ethyl 5,7-dichloro-N-(3,4-dichlorobenzyl)indole-2-carboxylate; M/z (+) 415 (M+), 159.

EXAMPLE 2.15

Ethyl 7-chloro-N-(3,4-dichlorobenzyl)indole-2-carboxylate; M/z (+) 381 (M+), 335, 308, 300, 159.

EXAMPLE 2.16

Diethyl N-(3,4-dichlorobenzyl)indole-2,5-dicarboxylate; M/z (+) 420 (M+), 391, 279, 167, 149.

EXAMPLE 2.17

Ethyl N-(3,4-dichlorobenzyl)-7-methoxyindole-2-carboxylate; M/z (+) 378 (M+), 279, 167, 149.

EXAMPLE 2.18

Ethyl 6-bromo-N-(3,4-dichlorobenzyl)indole-2-carboxylate; M/z (+) 425 (M+), 159.

EXAMPLE 2.19

Ethyl N-(3,4-dichlorobenzyl)-5-trifluoromethoxyindole-2-carboxylate; M/z (+) 431 (M+), 159.

EXAMPLE 2.20

Ethyl N-(3,4-dichlorobenzyl)-5-methylindole-2-carboxylate; M/z (+) 362 (M+), 279, 167, 149.

EXAMPLE 2.21

Ethyl N-(3,4-dichlorobenzyl)-4,6-bis-trifluoromethylindole-2-carboxylate; M/z (+) 483 (M+), 437, 402, 374, 340, 159.

EXAMPLE 2.22

Ethyl N-(3,4-dichlorobenzyl)-5-methanesulphonylindole-2-carboxylate; M/z (+) 425 (M+), 159.

EXAMPLE 2.23

Ethyl 4,7-dichloro-N-(3,4-dichlorobenzyl)indole-2-carboxylate; M/z (+) 415 (M+), 159.

EXAMPLE 2.24

Ethyl 7-acetyl-N-(3,4dichlorobenzyl)indole-2-carboxylate; M/z (+) 390 (M+), 232.

EXAMPLE 2.25

Ethyl 5-t-butyl-N-(3,4-dichlorobenzyl)indole-2-carboxylate; M/z (+) 404 (M+), 391, 279, 242, 167, 149.

EXAMPLE 2.26

Ethyl 6,7-dichloro-N-(3,4-dichlorobenzyl)indole-2-carboxylate; M/z (+) 415 (M+), 371, 344, 334, 159.

EXAMPLE 2.27

Ethyl N-(3,4-dichlorobenzyl)-7-methylindole-2-carboxylate; M/z (+) 362 (M+), 279, 167, 149.

EXAMPLE 2.28

Ethyl N-(3,4-dichlorobenzyl)-6-trifluoromethylindole-2-carboxylate; M/z (+) 415 (M+), 159.

EXAMPLE 2.29

Ethyl 5,6-dichloro-N-(3,4-dichlorobenzyl)indole-2-carboxylate; M/z (+) 415 (M+), 159.

EXAMPLE 2.30

Ethyl 3-chloro-N-(3,4dichlorobenzyl)-5-fluoroindole-2-carboxylate in 81% yield; NMR δ($CD_3SOCD_3$) 1.26 (t, 3H), 4.32 (q, 2H), 5.79 (s, 2H), 6.88 (dd, 1H), 7.28–7.39 (m, 2H), 7.44 (dd, 1H), 7.52 (d, 1H), 7.73 (dd, 1H).

EXAMPLE 2.31

Methyl 4-acetoxy-N-(3,4-dichlorobenzyl)indole-2-carboxylate in 91% yield; NMR δ($CD_3SOCD_3$) 2.36 (s, 3H), 3.8 (s, 3H), 5.81 (s, 2H), 6.92 (d, 2H), 7.28–7.37 (m, 3H), 7.51 (t, 2H); M/z (+) 394 (MH+), 392.

EXAMPLE 2.32

Methyl 4acetoxy-N-(3,4-difluorobenzyl)indole-2-carboxylate in 66% yield; NMR δ($CD_3SOCD_3$) 2.49 (s, 3H), 3.96 (s, 3H), 5.94 (s, 2H), 6.93–7.0 (m, 1H), 7.04 (d, 1H), 7.23–7.33 (m, 1H), 7.36–7.49 (d, 1H); M/z (+) 360 (MH+), 318.

EXAMPLE 2.33

Methyl 4-acetoxy-N-(4-chlorobenzyl)indole-2-carboxylate in 27% yield; NMR δ($CD_3SOCD_3$) 2.37 (s, 3H), 3.81 (s, 3H), 5.81 (s, 2H), 6.90 (d, 1H), 7.06 (d, 2H), 7.12 (m, 4H), 7.49 (d, 1H); M/z (+) 360 (MH+), 358.

EXAMPLE 2.34

Methyl 4acetoxy-N-(3-chlorobenzyl)indole-2-carboxylate in 88% yield; NMR δ($CD_3SOCD_3$) 2.28 (s, 3H), 3.74 (s, 3H), 5.75 (s, 2H), 6.8–6.9 (m, 2H), 7.04 (s, 1H), 7.16–7.27 (m, 4H), 7.38 (d, 1H); M/z (+) 358 (M+), 316.

EXAMPLE 2.35

Ethyl 3-amino-N-(3,4-dichlorobenzyl)indole-2-carboxylate in 44% yield; NMR δ($CD_3SOCD_3$) 1.21 (t, 3H), 4.21 (q, 2H), 5.56 (s, 2H), 6.0 (s, 2H), 6.86 (dd, 1H), 6.98 (t, 1H), 7.23 (d, 1H), 7.29 (t, 1H), 7.4 (d, 1H), 7.48 (d, 1H), 7.85 (d, 1H); M/z (+) 363 (M+).

EXAMPLE 2.36

Ethyl 4-amino-N-(3,4-dichlorobenzyl)indole-2-carboxylate in 61% yield; NMR δ($CD_3SOCD_3$) 1.25 (t, 3H), 4.25 (q, 2H), 5.7 (2 x s, 4H), 6.2 (d, 1H), 6.6 (d, 1H), 6.9 (d, 1H), 7.0 (dd, 1H), 7.25 (s, 1H), 7.5 (d, 1H), 7.6 (s, 1H); M/z (+) 365 (MH+), 363.

EXAMPLE 3

N-(3-chlorobenzyl)indole-2-carboxylic acid

Ethyl N-(3-chlorobenzyl)indole-2-carboxylate (0.47 g) was dissolved in THF/MeOH (1:1) and sodium hydroxide (2M, 4.5 ml) was added and the reaction stirred for 16 hours. The reaction was then concentrated in vacuo to dryness and the residue dissolved in water. The solution was acidified to pH 3 by dropwise addition of acetic acid, resulting in the precipitation of a white solid which was filtered off, washed with water and dried in vacuo to give the desired end product (0.35 g, 82%), mp 188–189°; NMR δ($CD_3SOCD_3$) 5.85 (s, 2H), 6.90 (d, 1H), 7.1 (m, 2H), 7.3 (m, 4H), 7.55 (d, 1H), 7.70 (d, 1H); M/z (−) 284 (M−H$^+$).

EXAMPLE 3.01–3.66

The procedure described in example 3 was repeated using the appropriate indole-2-carboxylic ester. Thus there were obtained the compounds described below.

EXAMPLE 3.01

N-(4-Chlorobenzyl)indole-2-carboxylic acid in 85% yield, mp 206–207°; NMR δ($CD_3SOCD_3$) 5.85 (s, 2H), 7.00 (d, 2H), 7.1 (t, 1H), 7.3 (m, 4H), 7.55 (d, 1H), 7.70 (d, 1H); M/z (−) 284 (M−H$^+$).

EXAMPLE 3.02

N-(3,4-Dichlorobenzyl)indole-2-carboxylic acid in 77% yield, mp 198–198°; NMR δ($CD_3SOCD_3$) 5.85 (s, 2H), 6.9 (d, 2H), 7.1 (t, 1H), 7.3 (m, 3H), 7.5 (t, 2H), 7.70 (d, 1H); M/z (−) 318 (M−H$^+$).

EXAMPLE 3.03

N-(3,4-Dichlorobenzyl)-5-nitroindole-2-carboxylic acid in 27% yield, mp 275–276°; NMR δ($CD_3SOCD_3$) 5.93 (s, 2H), 6.90 (dd, 1H), 7.38 (d, 1H), 7.52 (d, 1H), 7.80 (d, 1H), 8.14 (dd, 1H), 8.78 (d, 1H); M/z (−) 365 (M$^+$), 363, 319, 175, 159, 139, 108.

EXAMPLE 3.04

5-Bromo-N-(3,4-dichlorobenzyl)indole-2-carboxylic acid in 70% yield, mp 232–233°; NMR δ($CD_3SOCD_3$) 5.83 (s, 2H), 7.80 (dd, 1H), 7.23–7.58 (m, 5H), 7.90 (s, 1H); M/z (−) 399 (M$^+$), 398, 354, 145.

EXAMPLE 3.05

N-(3,4-Dichlorobenzyl)-5-phenylindole-2-carboxylic acid in 84% yield; NMR δ($CD_3SOCD_3$)5.88 (s, 2H), 6.95 (d, 1H), 7.20–7.70 (m, 10H), 7.95 (s, 1H); M/z (−) 396 (M$^+$), 394, 350.

EXAMPLE 3.06

N-(3,4-Dichlorobenzyl)-5-(N-morpholino)indole-2-carboxylic acid in 73% yield; NMR δ($CD_3SOCD_3$) 3.02 (t, 4H), 3.73 (t, 4H), 5.80 (s, 2H), 6.92 (d, 1H), 7.12 (m, 3H), 7.29 (s, 1H), 7.40 (d, 1H), 7.52 (d, 1H); M/z (−) 405 (M$^+$), 364.

EXAMPLE 3.07

N-(3,4-Dichlorobenzyl)-5-(N-pyrrolidino)indole-2-carboxylic acid in 28% yield; M/z (−) 389 (M$^+$).

EXAMPLE 3.08

N-(3,4-Dichlorobenzyl)-5-phenoxyindole-2-carboxylic acid in 83% yield; M/z (−) 412 (M$^+$).

EXAMPLE 3.09

N-(3,4-Dichlorobenzyl)-5-(4-dimethylaminophenyl)indole-2-carboxylic acid in 83% yield; M/z (−) 439 (M$^+$).

EXAMPLE 3.10

N-(3,4-Dichlorobenzyl)-5-methoxy-3-(trans-2-carboxycyclopropan-1-yl)-indole-2-carboxylic acid in 81% yield; NMR δ($CDCl_3$) 1.39 (m, 1H), 1.77 (m, 1H), 1.92 (m, 1H), 2.80 (m, 1H), 3.83 (s, 3H), 3.88 (s, 3H), 5.64(s, 2H), 6.80–7.30 (m, 6H); M/z (−)434 (M$^+$), 432.

EXAMPLE 3.11

N-(3-Methylbenzyl)-5-nitroindole-2-carboxylic acid in 56% yield (2 steps); M/z (−) 309 (M−H$^+$), 265.

EXAMPLE 3.12

N-(3-Chlorobenzyl)-5-nitroindole-2-carboxylic acid in 51% yield (2 steps); M/z (−) 329 (M−H$^+$), 285.

EXAMPLE 3.13

N-(3-Methoxybenzyl)-5-nitroindole-2-carboxylic acid in 22% yield (2 steps); M/z (−) 325 (M−H$^+$), 281, 205, 161.

EXAMPLE 3.14

5-Nitro-N-(3-trifluoromethylbenzyl)-indole-2-carboxylic acid in 56% yield (2 steps); M/z (−) 363 (M−H$^+$), 319.

EXAMPLE 3.15

N-(4-Methoxybenzyl)-5-nitroindole-2-carboxylic acid in 36% yield (2 steps); M/z (−) 325 (M−H$^+$), 281, 205, 161, 151, 107.

EXAMPLE 3.16

N-(3-Nitrobenzyl)-5-nitroindole-2-carboxylic acid in 43% yield (2 steps); M/z (−)340 (M−H$^+$), 296.

EXAMPLE 3.17

N-([5-Chloro-thien-2-yl]methyl)-5-nitroindole-2-carboxylic acid in 65% yield (2 steps); M/z (−) 335 (M−H$^+$), 255, 161.

EXAMPLE 3.18

5-Nitro-N-(4-trifluoromethoxybenzyl)indole-2-carboxylic acid in 49% yield (2 steps); M/z (−) 379 (M−H$^+$), 335.

EXAMPLE 3.19

5-Fluoro-N-(3-methylbenzyl)indole-2-carboxylic acid in 15% yield (2 steps); M/z (−) 282 (M−H$^+$), 238, 146.

EXAMPLE 3.20

N-(3-Chlorobenzyl)-5-fluoroindole-2-carboxylic acid in 87% yield (2 steps); M/z (−) 302 (M−H$^+$), 258.

EXAMPLE 3.21

5-Fluoro-N-(3-methoxybenzyl)indole-2-carboxylic acid in 83% yield (2 steps); M/z (−) 298 (M−H$^+$), 254, 146.

EXAMPLE 3.22

5-Fluoro-N-(3-trifluoromethylbenzyl)indole-2-carboxylic acid in 100% yield (2 steps); M/z (−) 336 (M−H$^+$), 292.

EXAMPLE 3.23

5-Fluoro-N-(4-methoxybenzyl)indole-2-carboxylic acid in 73% yield (2 steps); M/z (−) 298 (M−H$^+$), 254.

EXAMPLE 3.24

5-Fluoro-N-(3-nitrobenzyl)indole-2-carboxylic acid in 100% yield (2 steps); M/z (−) 313 (M−H$^+$), 269.

EXAMPLE 3.25

N-([5-Chloro-thien-2-yl]methyl)-5-fluoroindole-2-carboxylic acid in 53% yield (2 steps); M/z (−) 308 (M−H$^+$), 228.

EXAMPLE 3.26

N-(6-Chloropiperonyl)-5-fluoroindole-2-carboxylic acid in 100% yield (2 steps); M/z (−) 346 (M−H$^+$), 302, 272.

EXAMPLE 3.27

5-Fluoro-N-(4-trifluoromethoxybenzyl)indole-2-carboxylic acid in 21% yield (2 steps); M/z (−) 352 (M−H$^+$), 308.

EXAMPLE 3.28

N-(3-Chlorobenzyl)-6-fluoroindole-2-carboxylic acid in 44% yield (2 steps); M/z (−) 302 (M−H$^+$), 258.

EXAMPLE 3.29

6-Fluoro-N-(3-methoxybenzyl)indole-2-carboxylic acid in 45% yield (2 steps); M/z (−) 298 (M−H$^+$), 254.

EXAMPLE 3.30

6-Fluoro-N-(3-trifluoromethylbenzyl)indole-2-carboxylic acid in 58% yield (2 steps); M/z (−) 336 (M−H$^+$), 292.

EXAMPLE 3.31

6-Fluoro-N-(4-methoxybenzyl)indole-2-carboxylic acid in 52% yield (2 steps); M/z (−) 298 (M−H$^+$), 254.

EXAMPLE 3.32

6-Fluoro-N-(3-nitrobenzyl)indole-2-carboxylic acid in 72% yield (2 steps); M/z (−) 313 (M−H$^+$), 269.

EXAMPLE 3.33

N-([5-Chloro-thien-2-yl]methyl)-6-fluoroindole-2-carboxylic acid in 67% yield (2 steps); M/z (−) 308 (M−H$^+$), 228.

EXAMPLE 3.34

N-(6-Chloropiperonyl)-6-fluoroindole-2-carboxylic acid in 64% yield (2 steps); M/z (−) 346 (M−H$^+$), 302.

EXAMPLE 3.35

6-Fluoro-N-(4-trifluoromethoxybenzyl)indole-2-carboxylic acid in 55% yield (2 steps); M/z (−) 352 (M−H$^+$), 308.

EXAMPLE 3.36

N-(3-Chlorobenzyl)-4,6-dimethoxyindole-2-carboxylic acid in 99% yield (2 steps); M/z (−) 344 (M−H$^+$), 300.

EXAMPLE 3.37

4,6-Dimethoxy-N-(3-trifluoromethylbenzyl)indole-2-carboxylic acid in 96% yield (2 steps); M/z (−) 378 (M−H$^+$), 334.

EXAMPLE 3.38

N-([5-Chloro-thien-2-yl]methyl)-4,6-dimethoxyindole-2-carboxylic acid in 92% yield (2 steps); M/z (−) 350 (M−H$^+$), 270.

EXAMPLE 3.39

4,6-Dimethoxy-N-(4-trifluoromethoxybenzyl)indole-2-carboxylic acid in 88% yield (2 steps); M/z (−) 394 (M−H$^+$), 350.

EXAMPLE 3.40

5,6-Dimethoxy-N-(3-methylbenzyl)indole-2-carboxylic acid in 66% yield (2 steps); M/z (−) 324 (M−H$^+$), 280.

EXAMPLE 3.41

N-(3-Chlorobenzyl)-5,6-dimethoxyindole-2-carboxylic acid in 76% yield (2 steps); M/z (−) 344 (M−H$^+$), 300.

EXAMPLE 3.42

5,6-Dimethoxy-N-(3-trifluoromethylbenzyl)indole-2-carboxylic acid in 66% yield (2 steps); M/z (−) 378 (M−H$^+$), 334.

EXAMPLE 3.43

3-Bromo-N-(3-methylbenzyl)indole-2-carboxylic acid in 100% yield (2 steps); M/z (−) 344 (M−H$^+$), 342, 300, 298.

EXAMPLE 3.44

3-Bromo-N-(3-chlorobenzyl)indole-2-carboxylic acid in 92% yield (2 steps); M/z (−) 364 (M−H$^+$), 362, 320, 318.

EXAMPLE 3.45

3-Bromo-N-(3-methoxybenzyl)indole-2-carboxylic acid in 85% yield (2 steps); M/z (−) 360 (M−H$^+$), 358, 316, 314, 195.

EXAMPLE 3.46

3-Bromo-N-(3-trifluoromethylbenzyl)indole-2-carboxylic acid in 91% yield (2 steps); M/z (−) 396 (M−H$^+$), 354, 352.

EXAMPLE 3.47

3-Bromo-N-(4-methoxybenzyl)indole-2-carboxylic acid in 54% yield (2 steps); M/z (−) 358 (M−H$^+$), 316, 314.

EXAMPLE 3.48

3-Bromo-N-(3-nitrobenzyl)indole-2-carboxylic acid in 59% yield (2 steps); M/z (−) 373 (M−H$^+$), 331, 329, 249.

EXAMPLE 3.49

3-Bromo-N-([5-Chloro-thien-2-yl]methyl)indole-2-carboxylic acid in 82% yield (2 steps); M/z (−) 370 (M−H$^+$), 368, 290, 288.

EXAMPLE 3.50

3-Bromo-N-(6-chloropiperonyl)indole-2-carboxylic acid in 55% yield (2 steps); M/z (−) 408 (M−H$^+$), 406, 196, 194.

EXAMPLE 3.51

3-Bromo-N-(4-trifluoromethoxybenzyl)indole-2-carboxylic acid in 24% yield (2 steps); M/z (−) 414 (M−H$^+$), 412, 370, 368.

EXAMPLE 3.52

N-(3,4-Dichlorobenzyl)-4-phenylindole-2-carboxylic acid in 62% yield; M/z 396 (M$^+$), 394, 352, 350, 213.

EXAMPLE 3.53

N-(3,4-Dichlorobenzyl)-4-(4-dimethylaminophenyl) indole-2-carboxylic acid in 73% yield; M/z 439 (M$^+$), 437, 395, 393.

EXAMPLE 3.54

N-(3,4-Dichlorobenzyl)-4-(thien-2-yl)indole-2-carboxylic acid in 36% yield; M/z 402 (M$^+$), 400, 358, 356, 320, 318, 276, 274.

EXAMPLE 3.55

N-(3,4-Dichlorobenzyl)-5-(thien-2-yl)indole-2-carboxylic acid in 54% yield; M/z 402 (M$^+$), 400, 358, 356, 212, 113.

EXAMPLE 3.56

N-(3,4-Dichlorobenzyl)-6-(thien-2-yl)indole-2-carboxylic acid in 57% yield; 30 M/z 402 (M$^+$), 400, 358, 356, 322.

EXAMPLE 3.57

N-(3,4-Dichlorobenzyl)-5-methoxyindole-2-carboxylic acid in 76% yield, mp 206–207°; M/z 350 (M$^+$), 348, 306, 304.

EXAMPLE 3.58

N-(3,4-Dichlorobenzyl)-3-(trans-2-carboxy-cyclopropyl) indole-2-carboxylic acid in 60% yield, mp 184–185°; M/z 404 (M$^+$), 402, 360, 358.

EXAMPLE 3.59

5-Chloro-N-(3,4-dichlorobenzyl)indole-2-carboxylic acid in 79% yield, mp 227–228°; NMR δ(CD$_3$SOCD$_3$) 5.82 (s, 2H), 6.89 (d, 1H), 7.28 (m, 3H), 7.49 (d, 1H), 7.58 (d, 1H), 7.77 (s, 1H); M/z 354 (M$^+$), 352, 308, 145.

EXAMPLE 3.60

6-Chloro-N-(3,4-dichlorobenzyl)indole-2-carboxylic acid in 68% yield, mp 219–220°; M/z 354 (M$^+$), 352, 310, 308, 145.

EXAMPLE 3.61

N-(3,4-Dichlorobenzyl)-4-methoxyindole-2-carboxylic acid in 58% yield, mp 220–221°; M/z 350 (M$^+$), 348, 306, 304.

EXAMPLE 3.62

N-(3,4-Dichlorobenzyl)-6-trifluoromethylindole-2-carboxylic acid in 52% yield, mp 238–239°; M/z 388 (M$^+$), 386, 344, 342, 196.

EXAMPLE 3.63

N-(3,4-Dichlorobenzyl)-6-methoxyindole-2-carboxylic acid in 74% yield, mp 165–166°; M/z 350 (M$^+$), 348, 306, 304.

EXAMPLE 3.64

N-(3,4-Dichlorobenzyl)-6-nitroindole-2-carboxylic acid in 78% yield, mp 256–257°; M/z 365 (M$^+$), 363, 321, 319, 173, 145.

EXAMPLE 3.65

N-(3,4-Dichlorobenzyl)-4-nitroindole-2-carboxylic acid in 39% yield, mp 296–297°; M/z 365 (M$^+$), 363, 321, 319, 173, 145.

EXAMPLE 3.66

N-(3,4-Dichlorobenzyl)-5-(carboxymethylamino)indole-2-carboxylic acid in 55% yield, mp 206–207°; M/z (−) 393 (M$^+$), 391, 347, 333, 226, 139.

EXAMPLE 3.67

5,7-Dichloro-N-(3,4-dichlorobenzyl)indole-2-carboxylic acid in 32% yield (2 steps); M/z (−) 388 (M$^+$), 344.

EXAMPLE 3.68

7-Chloro-N-(3,4-dichlorobenzyl)indole-2-carboxylic acid in 81% yield (2 steps); M/z (−) 354 (M$^+$), 308.

EXAMPLE 3.69

N-(3,4-Dichlorobenzyl)indole-2,5-dicarboxylic acid in 49% yield (2 steps); M/z (−) 364 (M$^+$), 362, 332, 318, 202, 180.

EXAMPLE 3.70

N-(3,4-Dichlorobenzyl)-7-methoxyindole-2-carboxylic acid in 66% yield (2 steps); M/z (−) 350 (M$^+$), 348, 304.

EXAMPLE 3.71

6-Bromo-N-(3,4-dichlorobenzyl)indole-2-carboxylic acid in 79% yield (2 steps); M/z (−) 398 (M$^+$), 354.

EXAMPLE 3.72

N-(3,4-Dichlorobenzyl)-5-trifluoromethoxyindole-2-carboxylic acid in 68% yield (2 steps); M/z (−) 404 (M$^+$), 402, 358.

EXAMPLE 3.73

N-(3,4-Dichlorobenzyl)-5-methylindole-2-carboxylic acid in 59% yield (2 steps); M/z (−) 334 (M$^+$), 332, 288.

EXAMPLE 3.74

N-(3,4-Dichlorobenzyl)-4,6-bis-trifluoromethylindole-2-carboxylic acid in 62% yield (2 steps); M/z (−) 456 (M$^+$), 454, 410.

EXAMPLE 3.75

N-(3,4-Dichlorobenzyl)-5-methanesulphonylindole-2-carboxylic acid in 74% yield (2 steps); M/z (−) 398 (M$^+$), 396, 352.

EXAMPLE 3.76

4,7-Dichloro-N-(3,4-dichlorobenzyl)indole-2-carboxylic acid in 76% yield (2 steps); M/z (−) 389 (M$^+$), 344.

EXAMPLE 3.77

7-Acetyl-N-(3,4-dichlorobenzyl)indole-2-carboxylic acid in 57% yield (2 steps); M/z (−) 362 (M$^+$), 360, 316.

EXAMPLE 3.78

5-t-Butyl-N-(3,4-dichlorobenzyl)indole-2-carboxylic acid in 59% yield (2 steps); M/z (−) 376 (M$^+$), 374, 330.

EXAMPLE 3.79

6,7-Dichloro-N-(3,4-dichlorobenzyl)indole-2-carboxylic acid in 86% yield (2 steps); M/z (−) 388 (M$^+$), 386, 344, 342.

EXAMPLE 3.80

N-(3,4-Dichlorobenzyl)-7-methylindole-2-carboxylic acid in 55% yield (2 steps); M/z (−) 334 (M$^+$), 332, 290, 288.

EXAMPLE 3.81

N-(3,4-Dichlorobenzyl)-6-trifluoromethylindole-2-carboxylic acid in 74% yield (2 steps); M/z (−) 388 (M$^+$), 386, 344, 342.

EXAMPLE 3.82

5,6-Dichloro-N-(3,4-dichlorobenzyl)indole-2-carboxylic acid in 76% yield (2 steps); M/z (−) 388 (M$^+$), 386, 344, 342.

EXAMPLE 3.83

N-(3,4-Dichlorobenzyl)-3-methylindole-2-carboxylic acid in 84% yield; NMR δ(CD$_3$SOCD$_3$) 2.55 (s, 3H), 5.8 (s, 2H), 6.85 (d, 1H), 7.1 (t, 1H), 7.3 (m, 2H), 7.5 (m, 2H), 7.7 (m, 1H). M/z (−) 332 (M−H$^+$).

EXAMPLE 3.84

3-Acetyl-N-(3,4-Dichlorobenzyl)indole-2-carboxylic acid in 46% yield, mp 163–164°; NMR δ(CD$_3$SOCD$_3$) 2.65 (s, 3H), 5.6 (s, 2H), 7.05 (m, 1H), 7.3 (m, 2H), 7.5 (m, 1H), 7.6 (m, 3H), 8.05 (m, 1H). M/z (−) 362 (M$^+$).

EXAMPLE 3.85

5-Acetyl-N-(3,4-Dichlorobenzyl)indole-2-carboxylic acid in 92% yield, mp 261–262°; NMR δ(CD$_3$SOCD$_3$) 2.6 (s, 3H), 5.9 (s, 2H), 6.9 (m, 1H), 7.3 (m, 1H), 7.5 (m, 2H), 7.65 (d, 1H), 7.9 (m, 1H), 8.45 (m, 1H). M/z (−) 360 (M−H$^+$).

EXAMPLE 3.86

N-(3,4-Dichlorobenzyl)-4-hydroxyindole-2-carboxylic acid in 81% yield; NMR δ(CD$_3$SOCD$_3$) 5.78 (s, 2H), 6.43 (d, 1H), 6.88–6.94 (m, 2H), 7.08 (t, 1H), 7.27 (d, 1H), 7.36 (s, 1H), 7.52 (d, 1H), 9.89 (s, 1H); M/z (−) 336 (M$^+$), 334, 292, 290.

EXAMPLE 3.87

N-(3,4-Dichlorobenzyl)-4-trifluoromethylindole-2-carboxylic acid in 85% yield; M/z (−) 388 (M$^+$).

EXAMPLE 3.88

N-(3,4-Dichlorobenzyl)-5-trifluoromethylindole-2-carboxylic acid in 79% yield; M/z (−) 388 (M$^+$).

EXAMPLE 3.89

N-(3,4-Dichlorobenzyl)-7-trifluoromethylindole-2-carboxylic acid in 82% yield; M/z (−) 388 (M$^+$).

EXAMPLE 3.90

4-Chloro-N-(3,4-dichlorobenzyl)indole-2-carboxylic acid in 60% yield; M/z (−) 354 (M$^+$).

EXAMPLE 3.91

4,5-Dichloro-N-(3,4-dichlorobenzyl)indole-2-carboxylic acid in 87% yield; M/z (−) 389 (M$^+$).

EXAMPLE 3.92

N-(3,4-Dichlorobenzyl)-4-fluoroindole-2-carboxylic acid in 71% yield; M/z (−) 338 (M$^+$).

EXAMPLE 3.93

N-(3,4-Dichlorobenzyl)-6-fluoroindole-2-carboxylic acid in 95% yield; M/z (−) 338 (M$^+$).

EXAMPLE 3.94

N-(3,4-Dichlorobenzyl)-7-fluoroindole-2-carboxylic acid in 87% yield; M/z (−) 338 (M$^+$).

EXAMPLE 3.95

7-Bromo-N-(3,4-dichlorobenzyl)indole-2-carboxylic acid in 63% yield; M/z (−) 399 (M$^+$).

EXAMPLE 3.96

N-(3,4-Dichlorobenzyl)-4-(3-trifluoromethylphenyl)indole-2-carboxylic acid in 68% yield; M/z (−) 462 (M−H$^+$).

EXAMPLE 3.97

N-(3,4-Dichlorobenzyl)-4-(4-trifluoromethylphenyl)indole-2-carboxylic acid in 85% yield; M/z (−) 462 (M−H$^+$).

EXAMPLE 3.98

N-(3,4-Dichlorobenzyl)-4-(2-fluorophenyl)indole-2-carboxylic acid in 45% yield; M/z (−) 412 (M−H$^+$).

EXAMPLE 3.99

N-(3,4-Dichlorobenzyl)-4-(3-methylphenyl)indole-2-carboxylic acid in 65% yield; M/z (−) 408 (M−H$^+$).

EXAMPLE 3.100

4-(3-Aminophenyl)-N-(3,4-dichlorobenzyl)indole-2-carboxylic acid in 51% yield; M/z (−) 409 (M−H$^+$).

EXAMPLE 3.101

4-(4-Chlorophenyl)-N-(3,4-dichlorobenzyl)indole-2-carboxylic acid in 65% yield; M/z (−) 428 (M−H$^+$).

EXAMPLE 3.102

N-(3,4-Dichlorobenzyl)-4-(4-methoxyphenyl)indole-2-carboxylic acid in 83% yield; M/z (−) 424 (M−H$^+$).

EXAMPLE 3.103

N-(3,4-Dichlorobenzyl)-4-(2-napthyl)indole-2-carboxylic acid in 84% yield; M/z (−) 444 (M−H$^+$).

EXAMPLE 3.104

4-(5-Chlorothien-2-yl)-N-(3,4-dichlorobenzyl)indole-2-carboxylic acid in 78% yield; M/z (−) 434 (M−H$^+$).

EXAMPLE 3.105

N-(3,4-Dichlorobenzyl)-4-(thien-3-yl)indole-2-carboxylic acid in 84% yield; M/z (−) 400 (M−H$^+$).

EXAMPLE 3.106

N-(3,4-Dichlorobenzyl)-4-(2-pyridyl)indole-2-carboxylic acid in 70% yield; M/z (−) 397 (M$^+$).

EXAMPLE 3.107

N-(3,4-Dichlorobenzyl)-4-(3-pyridyl)indole-2-carboxylic acid in 50% yield; M/z (−) 397 (M$^+$).

EXAMPLE 3.108

3-Bromo-5-chloro-N-(3,4-dichlorobenzyl)indole-2-carboxylic acid in 93% yield; NMR δ(CD$_3$SOCD$_3$) 5.82 (s, 2H), 6.91 (dd,1H), 7.3–7.4 (m, 2H), 7.52 (d, 1H), 7.56 (d, 1H), 7.66 (d, 1H); M/z (−) 430 (M−H$^+$), 386.

EXAMPLE 3.109

3-Chloro-N-(3,4-dichlorobenzyl)-5-fluoroindole-2-carboxylic acid in 94% yield; NMR δ(CD$_3$SOCD$_3$) 5.81 (s, 2H), 6.90 (dd, 1H), 7.24 (t, 1H), 7.34–7.40 (m, 2H), 7.67 (dd, 1H); M/z (+) 374 (M$^+$), 372, 370, 330, 328, 326.

EXAMPLE 3.110

5-Amino-N-(3,4-dichlorobenzyl)indole-2-carboxylic acid in 78% yield; NMR δ(CD$_3$SOCD$_3$) 5.70 (s, 2H), 6.70 (m, 2H), 6.88 (dd, 1H), 7.0 (s, 1H), 7.22 (m, 2H), 7.49 (d, 1H); M/z (−) 335, 333, 289.

EXAMPLE 3.111

4-Amino-N-(3,4-dichlorobenzyl)indole-2-carboxylic acid in 61% yield; M/z (−) 335, 333, 291, 289.

EXAMPLE 4

N-(3,4-Dichlorobenzyl)-5-acetylaminoindole-2-carboxylic acid

Methyl N-(3,4-Dichlorobenzyl)-5-acetylaminoindole-2-carboxylate (88 mg) and lithium iodide (300 mg) were dissolved in pyridine and heated at reflux for 8 hours, then cooled to room temperature and poured into 2M HCl and extracted with diethyl ether. Combined organic extracts were dried (MgSO$_4$) and concentrated in vacuo to give an oil which was purified by column chromatography using DCM-2% methanol as eluent to give the desired end product as a white solid (19 mg, 22%), mp 245–246°; NMR δ(CD$_3$SOCD$_3$) 2.02 (s, 3H), 5.82 (s, 2H), 6.90 (d, 1H), 7.20–7.55 (m, 5H), 8.02 (s, 1H), 9.83 (s, 1H); M/z(+) 377 (MH$^+$), 278.

EXAMPLE 5

Ethyl N-(3,4-dichlorobenzyl)-5-(4-[N,N-dimethylamino]phenyl)indole-2-carboxylate Ethyl 5-bromo-N-(3,4dichlorobenzyl)indole-2-carboxylate (0.3 g), 4-dimethylaminobenzene boronic acid (0.13 g) and tetrakis triphenylphosphine-palladium(0) (20 mg) were dissolved in degassed toluene/ethanol/2M potassium carbonate (2:2:1) under argon and warmed at 80° C. for 16 hours. The reaction was then cooled to room temperature and partitioned between 2M HCl and ethyl acetate. Combined organic extracts were dried (MgSO$_4$) and concentrated in vacuo. The residue was purified by column chromatography using i-hexane-15% ethyl acetate as eluent to give the desired end product as a pale brown solid (0.25 g, 76%); NMR δ(CDCl$_3$) 1.38 (t, 3H), 2.98 (s, 6H), 4.38 (q, 2H), 5.78 (s, 2H), 6.80–7.80 (m, 11H); M/z (+) 467 (M$^+$), 319, 280, 239.

EXAMPLES 5.01–5.05

The procedure described in example 5 was repeated using the appropriate bromoindole and boronic acid. Thus were obtained the compounds described below.

EXAMPLE 5.01

Ethyl N-(3,4-dichlorobenzyl)-4-phenyl)indole-2-carboxylate in 100% yield; M/z(+) 424 (M$^+$), 390, 130, 116.

EXAMPLE 5.02

Ethyl N-(3,4-dichlorobenzyl)-4-(4-[N,N-dimethylamino]phenyl)indole-2-carboxylate in 100% yield; M/z(+) 467 (M$^+$), 241, 198, 131, 130, 118.

EXAMPLE 5.03

Ethyl N-(3,4-dichlorobenzyl)-4-(thien-2-yl)indole-2-carboxylate in 79% yield; M/z(+) 430 (M$^+$), 350, 348, 215.

EXAMPLE 5.04

Ethyl N-(3,4-dichlorobenzyl)-5-(thien-2-yl)indole-2-carboxylate in 30% yield; M/z 430 (M$^+$), 398, 396, 350, 348, 130.

EXAMPLE 5.05

Ethyl N-(3,4-dichlorobenzyl)-6-(thien-2-yl)indole-2-carboxylate in 61% yield; M/z(+) 430 (M$^+$), 350, 348, 215.

EXAMPLE 5.06

Ethyl N-(3,4-dichlorobenzyl)-4-(3-trifluoromethylphenyl)indole-2-carboxylate in 87% yield; NMR δ(CD$_3$SOCD$_3$) 1.2 (t, 3H), 4.3 (q, 2H), 5.9 (s, 2H), 6.95 (m, 1H), 7.3 (m, 2H), 7.4 (m, 2H), 7.5 (m, 1H), 7.7 (m, 1H), 7.8 (m, 2H), 7.9 (s, 1H), 8.0 (m, 1H); M/z (+) 492 (M$^+$).

EXAMPLE 5.07

Ethyl N-(3,4-dichlorobenzyl)-4-(4-trifluoromethylphenyl)indole-2carboxylate in 81% yield; NMR δ(CD$_3$SOCD$_3$) 1.3 (t, 3H), 4.3 (q, 2H), 5.9 (s, 2H), 6.9 (m, 1H), 7.3 (d, 1H), 7.4 (m, 2H), 7.5 (m, 2H), 7.70 (d, 1H), 7.9 (s, 4H); M/z (+) 492 (M$^+$).

EXAMPLE 5.08

Ethyl N-(3,4-dichlorobenzyl)-4-(2-fluorophenyl)indole-2-carboxylate in 97% yield; NMR δ(CD$_3$SOCD$_3$) 1.25 (t, 3H), 4.3 (q, 2H), 5.9 (s, 2H), 6.9 (m, 1H), 7.1 (m, 1H), 7.2 (d, 1H), 7.4 (m, 7H), 7.7 (m, 1H); M/z (+) 442 (M$^+$).

EXAMPLE 5.09

Ethyl N-(3,4-dichlorobenzyl)-4-(3-methylphenyl)indole-2-carboxylate in 78% yield; NMR δ(CD$_3$SOCD$_3$) 1.25 (t, 3H), 2.4 (s, 3H), 4.25 (q, 2H), 5.85 (s, 2H), 6.9 (m, 1H), 7.1 (m, 1H), 7.2 (m, 2H), 7.3 (s, 1H), 7.4 (m, 5H), 7.5 (m, 2H); M/z (+) 438 (M$^+$).

EXAMPLE 5.10

Ethyl 4-(3-aminophenyl)-N-(3,4-dichlorobenzyl)indole-2-carboxylate in 52% yield; NMR δ(CD$_3$SOCD$_3$) 1.3 (t, 3H), 4.3 (q, 2H), 5.9 (s, 2H), 6.6 (m, 1H), 6.75 (m, 1H), 6.9 (m, 2H), 7.15 (m, 2H), 7.4 (m, 3H), 7.55 (t, 2H); M/z (+) 439 (M$^+$).

EXAMPLE 5.11

Ethyl 4-(4-chlorophenyl)-N-(3,4-dichlorobenzyl)indole-2-carboxylate in 81% yield; NMR δ(CD$_3$SOCD$_3$) 1.2 (t, 3H), 4.3 (q, 2H), 5.9 (s, 2H), 6.9 (m, 1H), 7.2 (d, 1H), 7.5 (m, 9H); M/z (+) 458 (MH$^+$).

EXAMPLE 5.12

Ethyl N-(3,4-dichlorobenzyl)-4-(4-methoxyphenyl)indole-2-carboxylate in 57% yield; NMR δ(CD$_3$SOCD$_3$) 1.25 (t, 3H), 3.8 (s, 3H), 4.3 (q, 2H), 5.9 (s, 2H), 6.9 (m, 1H), 7.1 (d, 1H), 7.4 (m, 3H), 7.6 (m, 4H); M/z (+) 454 (MH$^+$).

EXAMPLE 5.13

Ethyl N-(3,4-dichlorobenzyl)-4-(2-napthyl)indole-2-carboxylate in 78% yield; NMR δ(CD$_3$SOCD$_3$) 1.2 (t, 3H), 4.3 (q, 2H), 5.9 (s, 2H), 7.05 (m, 2H), 7.5 (m, 6H), 7.6 (m, 1H), 7.8 (m, 1H), 8.0 (m, 3H), 8.2 (s, 1H); M/z (+) 474 (MH$^+$).

EXAMPLE 5.14

Ethyl 4-(5-chlorothien-2-yl)-N-(3,4-dichlorobenzyl)indole-2-carboxylate in 18% yield; NMR δ(CD$_3$SOCD$_3$) 1.3 (t, 3H), 4.3 (q, 2H), 5.85 (s, 2H), 6.9 (m, 1H), 7.25 (m, 1H), 7.3 (m, 3H), 7.5 (m, 4H); M/z (+) 466 (MH$^+$).

EXAMPLE 5.15

Ethyl N-(3,4-dichlorobenzyl)-4-(thien-3-yl)indole-2-carboxylate in 73% yield; NMR δ(CD$_3$SOCD$_3$) 1.3 (t, 3H), 4.3 (q, 2H), 5.9 (s, 2H), 6.9 (m, 1H), 7.4 (m, 1H), 7.5 (m, 4H), 7.7 (m, 1H), 7.9 (m, 1H); M/z (+) 430 (MH +).

EXAMPLE 6

Ethyl N-(3,4-dichlorobenzyl)-4-(2-pyridyl)indole-2-carboxylate

Ethyl 4-bromo-N-(3,4-dichlorobenzyl)indole-2-carboxylate (0.15 g), 2-(tri-n-butylstannyl) pyridine (0.155 g), lithium chloride (30 mg) and tetrakis triphenylphosphine-palladium(0) (15 mg) were dissolved in anhydrous degassed toluene under argon and warmed at 105° C. for 16 hours. The reaction was then cooled to room temperature and partitioned between water and dichloromethane. Combined organic extracts were dried (MgSO$_4$) and concentrated in vacuo. The residue was purified by column chromatography using i-hexane-30% ethyl acetate as eluent to give the desired end product as a white solid (0.08 g, 54%); M/z (+) 425 (M$^+$).

EXAMPLE 6.01

The procedure described in example 6 was repeated using the appropriate bromoindole and aryl stannane. Thus was obtained the compound described below.

Ethyl N-(3,4-dichlorobenzyl)-4-(3-pyridyl)indole-2-carboxylate in 34% yield; M/z (+) 425 (M$^+$).

EXAMPLE 7

1-(3,4-Dichlorobenzyl)-N-(phenylsulphonyl)indole-2-carboxamide

A solution of N-(3,4-dichlorobenzyl)indole-2-carboxylic acid (0.23 g), benzenesulphonamide (129 mg), dimethylaminopyridine (0.22 g) and 1-ethyl-3-(3-dimethylaminopropyl)carbodiimide hydrochloride (0.19 g) in dichloromethane was allowed to stir for 24 hours at room temperature. 2N HCl was added and the reaction stirred vigorously for 2 hours, then extracted with dichloromethane. Combined organic extracts were dried (MgSO$_4$) and concentrated to yield the desired end product as a white crystalline solid (122 mg, 32%); NMR δ(CD$_3$SOCD$_3$) 5.65 (s, 2H), 6.73 (dd, 1H), 7.12 (m, 2H), 7.30 (t, 1H), 7.38 (d, 1H), 7.56 (m, 4H), 7.70 (m, 2H), 7.91 (d, 2H); M/z (−) 457 (M−H$^+$).

EXAMPLES 7.01–7.04

The procedure described in example 6 above was repeated using the appropriate amine or sulphonamide. Thus were obtained the products described below.

EXAMPLE 7.01

1-(3,4-Dichlorobenzyl)-N-(methanesulphonyl)indole-2-carboxamide in 44% yield; NMR δ(CD$_3$SOCD$_3$) 3.30 (s, 3H), 5.77 (s, 2H), 6.91 (dd, 1H), 7.16 (t, 1H), 7.33 (m, 2H), 7.51 (d, 1H), 7.56 (d, 1H), 7.60 (s, 1H), 7.74 (d, 1H); M/z (+) 397 (MH$^+$).

EXAMPLE 7.02

1-(3,4-Dichlorobenzyl)-N-(3,5-dimethylisoxazole4-sulphonyl)indole-2-carboxamide in 37% yield; NMR δ(CD$_3$SOCD$_3$) 2.32 (s, 3H), 2.62 (s, 3H), 5.68 (s, 2H), 6.77 (dd, 1H), 7.13 (s, 1H), 7.15 (t, 1H), 7.33 (t, 1H), 7.42 (d, 1H), 7.56 (s, 1H), 7.58 (d, 1H), 7.71 (d, 1H); M/z (−) 476 (M−H$^+$).

EXAMPLE 7.03

1-(3,4-Dichlorobenzyl)-2-(4-methylpiperazin-1-ylcarbonyl)indole in 10% yield; NMR δ(CD$_3$SOCD$_3$) 2.79 (s, 3H), 3.17 (s, 2H), 3.77 (s, 2H), 5.48 (s, 2H), 6.87 (s, 1H), 7.05 (dd, 1H), 7.11 (t, 1H), 7.23 (m, 1H), 7.35 (d, 1H), 7.45 (s, 1H), 7.49 (d, 1H), 7.65 (d, 1H); M/z (+) 476 (MH$^+$).

EXAMPLE 7.04

1-(3,4-Dichlorobenzyl)-N-methylindole-2-carboxamide in 54% yield; NMR δ(CD$_3$SOCD$_3$) 2.75 (d, 3H), 5.81 (s, 2H), 6.99 (dd, 1H), 7.10 (t, 1H), 7.14 (s, 1H), 7.22 (t, 1H), 7.32 (d, 1H), 7.50 (m, 2H), 7.66 (d, 1H), 8.53 (brs, 1H); M/z (−) 331 (M−H$^+$).

EXAMPLE 8

N-(3,4-Dichlorobenzyl)-2-cyanoindole and N-(3,4-dichlorobenzyl)indole-2-carboxamide Methanesulphonyl chloride (1 ml) added to a solution of N-(3,4-dichlorobenzyl)indole-2-carboxylic acid (0.23 g) in pyridine at 0° C., and reaction stirred for 2 hours. Ammonia gas was then bubbled through the reaction mixture for 15 mins and then concentrated in vacuo. The residue was dissolved in fresh pyridine, cooled to 0° C. and methanesulphonyl chloride (1 ml) added dropwise. The reaction was stirred for 16 hours, then concentrated in vacuo and residue partitioned between 1N HCl and dichloromethane. Combined organic extracts were dried (MgSO$_4$) and concentrated and the resulting solid purified by column chromatography using dichloromethane-10% ethyl acetate as eluent to give N-(3,4dichlorobenzyl)-2-cyanoindole as yellow crystals (58 mg, 27%); NMR δ(CD$_3$SOCD$_3$) 5.82 (s, 2H), 6.95–7.70 (m, 7H), 8.03 (m, 1H); M/z (+) 300 (M$^+$), 161, 159; followed by N-(3,4-dichlorobenzyl) indole-2-carboxamide as yellow crystals (37 mg, 16%); M/z (+) 318(M$^+$), 274, 161, 159,71, 57.

EXAMPLE 9

Ethyl 5-amino-N-(3,4-dichlorobenzyl)indole-2-carboxylate

Sodium borohydride (1.19 g) in ethanol was added dropwise to ethyl N-(3,4-dichlorobenzyl)-5-nitroindole-2-carboxylate (12.4 g) and stannous chloride dihydrate (35.6 g) in ethanol at 60° C. and reaction stirred for 5 hours. The mixture was then cooled, made basic with 2N sodium hydroxide and extracted with ethyl acetate. Combined organic extracts were dried (MgSO$_4$) and concentrated to give an oil which crystallised upon trituration with i-hexane. Filtration yielded the desired end product as a pale brown solid (1.18 g, 10%); NMR δ(CDCl$_3$) 1.32 (t, 3H), 4.26 (q, 2H), 6.69 (s, 2H), 6.78–7.35 (m, 7H); M/z (−) 363 (M$^+$), 274, 267, 265, 151, 121, 102.

The procedure described above was repeated using the appropriate nitroindole. Thus was obtained the compound described below.

EXAMPLE 9.1

Ethyl 4-amino-N-(3,4-dichlorobenzyl)indole-2-carboxylate in 43% yield; M/z (+) 364, 362, 203, 159, 131.

EXAMPLE 10

Methyl 5-acetylamino-N-(3,4-dichlorobenzyl)indole-2-carboxylate

Methyl N-(3,4-dichlorobenzyl)-5-aminoindole-2-carboxylate (0.28 g) was dissolved in acetic anhydride and heated to 90° C. for 1 hour. Upon cooling, the title compound crystallised as white needles, was filtered off, washed with diethyl ether and dried in vacuo to yield the desired end product (0.1 g, 32%); NMR δ(CD$_3$SOCD$_3$) 2.03 (s, 3H), 3.80 (s, 3H), 5.80 (s, 2H), 6.88 (m, 1H), 7.36 (m, 3H), 7.52 (d, 2H), 8.08 (s, 1H), 9.88 (s, 1H); M/z (−) 391 (M$^+$), 389.

EXAMPLE 11

Methyl N-(3,4-dichlorobenzyl)-5-(ethoxycarbonylmethylamino)indole-2-carboxylate

Sodium cyanoborohydride (0.2 g) was added in a single portion to methyl N-(3,4-dichlorobenzyl)-5-aminoindole-2-carboxylate (0.16 g), ethyl glyoxalate (0.2 ml of 50 wt % solution in toluene) and acetic acid (0.1 ml) in methanol (3 ml). The reaction was stirred for 5 mins then partitioned between ethyl acetate and 2M HCl. Combined organic extracts were dried (MgSO$_4$) and concentrated to give an oil which crystallised upon trituration with i-hexane. Filtration yielded the desired end product as an off-white powder (0.136 g, 67%); NMR δ(CD$_3$SOCD$_3$) 1.18 (t, 3H), 3.79 (s, 3H), 3.82 (d, 2H), 4.08 (q, 2H), 5.72 (s, 2H), 6.60–7.50 (m, 7H); M/z (+) 435 (M+), 133.

Preparation of Starting Materials

Starting materials for the Examples above are either commercially available or are readily prepared by standard methods from known materials. For example the following reactions (Methods A–J) are illustrations but not limitations of the preparation of some of the starting materials used in the above reactions.

Method A

Ethyl 5-(N-morpholino)indole-2-carboxylate

5-N-Morpholino-2-nitrotoluene (2 g) in THF was added dropwise to a solution of potassium ethoxide (1.12 g) and diethyl oxalate (1.8 ml) in THF to give a deep purple solution which was stirred for 16 hours then concentrated in vacuo. The residue was triturated with diethyl ether and filtered to give a purple solid which was dissolved in ethanol containing acetic acid (2 ml). Cyclohexene (2 ml) and 10% Pd/C (0.2 g) was added and the mixture heated at reflux for 18 hours, cooled to room temperature, filtered and concentrated in vacuo. The residue was triturated with diethyl ether and filtered to give the desired starting material as a pale brown solid in 50% yield; NMR δ(CD$_3$SOCD$_3$) 1.32 (t, 3H), 3.03 (t, 4H), 3.73 (t, 4H), 4.29 (q, 2H), 7.02 (m, 2H), 7.08 (d, 1H), 7.34 (d, 1H), 11.60 (brs, 1H); M/z (+) 275 (MH$^+$), 229.

The procedure described above was repeated using the appropriate 2-nitrotoluene. Thus were obtained the compounds described below.

Ethyl 5-N-pyrrolidinoindole-2-carboxylate in 21% yield; NMR δ(CD$_3$SOCD$_3$) 1.29 (t, 3H), 1.92 (t, 4H), 3.20 (t, 4H), 4.27 (q, 2H), 6.60 (d, 1H), 6.76 (dd, 1H), 6.91 (m, 1H) 7.29 (d, 1H), 11.40 (brs, 1H); M/z (+) 259 (MH$^+$).

Ethyl 5-phenoxyindole-2-carboxylate in 36% yield; NMR δ(CD$_3$SOCD$_3$) 1.32 (t, 3H), 4.33 (q, 2H), 6.90–7.48 (m, 9H), 11.85 (brs, 1H); M/z (+) 282 (MH$^+$), 240, 200, 198.

Intermediates used in preparation of these starting materials were prepared as follows.

5-N-Morpholino-2-nitrotoluene

A mixture of 5-fluoro-2-nitrotoluene (11 g), morpholine (8.1 ml), and potassium carbonate (12.8 g) in dimethylsulphoxide was heated and stirred at 100° C. for 3 hours then cooled to room temperature. The reaction was poured into water and the resulting yellow solid filtered off and recrystallized from methanol to give the desired starting material as yellow needles (13.4 g, 85%), mp 205–206°; NMR δ(CD$_3$SOCD$_3$) 3.28 (s, 3H), 3.37 (t, 4H), 3.71 (t, 4H), 6.87 (m, 2H), 8.00 (d, 1H); M/z (+) 223 (MH$^+$), 206.

The procedure described above was repeated using the appropriate amine or hydroxy compound. Thus were obtained the compounds described below.

5-N-Pyrrolidino-2-nitrotoluene in 90% yield; NMR δ(CD$_3$SOCD$_3$) 1.97 (m, 4H), 2.55 (s, 3H), 3.36 (m, 4H), 6.44 (m, 2H), 8.00 (d, 1H); M/z (+) 207 (MH$^+$), 190.

5-Phenoxy-2-nitrotoluene in 100% yield; NMR δ(CDCl$_3$) 2.58 (s, 3H), 6.83 (m, 2H), 7.08 (d, 2H), 7.24 (m, 1H), 7.42 (m, 2H), 8.04 (d, 1H); M/z (+) 230 (MH$^+$).

Method B

Ethyl 5-bromoindole-2-carboxylate

4-Bromophenylhydrazine hydrochloride (15 g), ethyl pyruvate (11 ml) and acetic acid (1 ml) were dissolved in ethanol and heated to reflux for 2 hours, then cooled to room temperature, resulting in precipitation of a yellow solid, which was filtered off and dried in vacuo to give the ethyl pyruvate 4-bromophenylhydrazone (16.3 g, 71%), mp 153–154°; NMR δ(CD$_3$SOCD$_3$) 1.23 (t, 3H), 2.03 (s, 3H), 4.18 (q, 2H), 7.19 (d, 2H), 7.40 (d, 2H), 9.88 (brs, 1H); M/z (−) 285 (M$^+$), 283, 171, 169, 113.

The powdered hydrazone was mixed with polyphosphoric acid (100 g) and the resulting paste heated at 110° C. for 1 hour, then cooled to room temperature. Water was added with stirring, and the resulting pale brown solid filtered off and recrystallized from ethanol to give the desired starting material as a yellow powder (5.80 g, 38%), mp 160–161°; NMR δ(CD$_3$SOCD$_3$) 1.42 (t, 3H), 4.42 (q, 2H), 7.14 (s, 1H), 7.73–7.40 (m, 2H), 9.21 (brs, 1H); M/z (−) 268 (M+), 266, 196, 194, 157.

The procedure described above was repeated using the appropriate hydrazine. Thus were obtained the compounds described below. (Note: where two regioisomeric products were formed, these were separated by column chromatography).

Ethyl 4-bromoindole-2-carboxylate in 5% yield (2 steps); NMR δ(CDCl$_3$) 1.43 (t, 3H), 4.42 (q, 2H), 7.12–7.40 (m, 4H), 9.20 (brs, 1H); M/z (−) 268 (M$^+$), 266, together with ethyl 6-bromoindole-2-carboxylate in 3% yield (2 steps); NMR δ(CDCl$_3$) 1.42 (t, 3H), 4.42 (q, 2H), 7.23 (m, 2H), 7.58 (d, 1H), 7.60 (s, 1H), 9.00 (brs, 1H); M/z (−) 268 (M$^+$), 266, 109.

Ethyl 4-nitroindole-2-carboxylate in 19% yield (2 steps), mp 225–226°; NMR δ(CDCl$_3$) 1.38 (t, 3H), 4.41 (q, 2H), 7.50 (t, 1H), 7.60 (s, 1H), 7.95 (d, 1H), 8.15 (d, 1H), 12.76 (brs, 1H), M/z (+) 235 (MH$^+$), together with ethyl 6-nitroindole-2-carboxylate in 21% yield (2 steps), mp 195–196°; NMR δ(CDCl$_3$) 1.37 (t, 3H), 4.39 (q, 2H), 7.31 (s, 1H), 7.88 (t, 1H), 7.94 (dd, 1H), 8.35 (d, 1H), 12.61 (brs, 1H); M/z (+) 235 (MH$^+$).

Ethyl 5,7-difluoroindole-2-carboxylate in 29% yield (2 steps); NMR δ(CD$_3$SOCD$_3$) 1.3 (t, 3H), 4.3 (q, 2H), 7.1–7.4 (m, 3H), 12.5 (bs, 1H).

Ethyl 4-trifluoromethylindole-2-carboxylate in 12% yield (2 steps), mp 147–148°; NMR δ(CD$_3$SOCD$_3$) 1.3 (t, 3H), 4.4 (q, 2H), 7.1 (s, 1H), 7.5 (m, 2H), 7.8 (d, 1H), 12.4 (bs, 1H); M/z (+) 257 (M$^+$), together with ethyl 6-trifluoromethylindole-2-carboxylate in 8% yield (2 steps), mp 181–182°; NMR δ(CD$_3$SOCD$_3$) 1.35 (t, 3H), 4.4 (q, 2H), 7.25 (s, 1H), 7.35 (m, 1H), 7.75 (d, 1H), 7.9 (d, 1H), 12.3 (bs, 1H); M/z (+) 257 (M$^+$).

Ethyl 5-t-butylindole-2-carboxylate in 21% yield (2 steps), mp 102–103°; NMR δ(CD$_3$SOCD$_3$) 1.3 (t+s, 12H), 4.3 (q, 2H), 7.05 (m, 1H), 7.35 (m, 2H), 7.6 (m, 1H), 11.7 (bs, 1H); M/z (+) 245 (M$^+$)).

Ethyl 4-methoxyindole-2-carboxylate in 2% yield (2 steps), mp 169–170°; NMR δ(CD$_3$SOCD$_3$) 1.3 (t, 3H), 3.85 (s, 3H), 4.3 (q, 2H), 6.5 (d, 1H), 7.0 (m, 2H), 7.2 (t, 1H); M/z (+) 219 (M$^+$), together with ethyl 6-methoxyindole-2-carboxylate in 26% yield (2 steps), mp 130–131°; NMR δ(CD$_3$SOCD$_3$) 1.3 (t, 3H), 3.85 (s, 3H), 4.3 (q, 2H), 6.85 (s, 1H), 7.05 (s, 1H), 7.5 (d, 1H); M/z (+) 219 (M$^+$).

Ethyl 4-chloroindole-2-carboxylate in 16% yield (2 steps), mp 141–142°; NMR δ(CD$_3$SOCD$_3$) 1.3 (t, 3H), 4.3 (q, 2H), 7.1 (s, 1H), 7.15 (d, 1H), 7.25 (t, 1H), 7.4 (d, 1H), 12.2 (bs, 1H); M/z (+) 223 (M$^+$), together with ethyl 6-chloroindole-2-carboxylate in 30% yield (2 steps), mp 173–174°; NMR δ(CD$_3$SOCD$_3$) 1.3 (t, 3H), 4.3 (q, 2H), 7.05 (d, 1H), 7.15 (s, 1H), 7.45 (s, 1H), 7.65 (d, 1H), 12.0 (bs, 1H); M/z (+) 223 (M$^+$).

Ethyl 7-chloroindole-2-carboxylate in 26% yield (2 steps), mp 104–105°; NMR δ(CD$_3$SOCD$_3$) 1.35 (t, 3H), 4.35 (q, 2H), 7.05 (t, 1H), 7.25 (s, 1H), 7.35 (d, 12.05 (bs, 1H); M/z (+) 223 (M$^+$).

Ethyl 5-methylindole-2-carboxylate in 1% yield (2 steps), mp 157–158°; NMR δ(CD$_3$SOCD$_3$) 1.3 (t, 3H), 2.35 (s, 3H), 4.3 (q, 2H), 7.05 (m, 2H), 7.35 (m, 2H), 11.7 (bs, 1H); M/z (+) 203 (M$^+$).

Ethyl 6,7-dichloroindole-2-carboxylate in 18% yield (2 steps), mp 134–135°; NMR δ(CD$_3$SOCD$_3$) 1.3 (t, 3H), 4.3 (q, 2H), 7.25 (s+d, 2H), 7.65 (d, 1H), 12.24 (bs, 1H); M/z (+) 257 (M$^+$).

Ethyl 5-methanesulphonylindole-2-carboxylate in 40% yield (2 steps), mp 161–162°; NMR δ(CD$_3$SOCD$_3$) 1.3 (t, 3H), 3.15 (s, 3H), 4.35 (q, 2H), 7.4 (s, 1H), 7.6 (1, dH), 7.75 (d, 1H), 8.3 (s, 1H), 12.4 (bs, 1H); M/z (+) 268 (MH$^+$).

Ethyl 7-methylindole-2-carboxylate in 13% yield (2 steps), mp 119–120°; NMR δ(CD$_3$SOCD$_3$) 1.35 (t, 3H), 2.5 (s, 3H), 4.35 (q, 2H), 6.95 (d, 1H), 7.05 (d, 1H), 7.15 (s, 1H), 7.45 (d, 1H), 11.6 (bs, 1H); M/z (+) 203 (M$^+$).

Ethyl 4,5-dichloroindole-2-carboxylate in 6% yield (2 steps), mp 204–205°; NMR δ(CD$_3$SOCD$_3$) 1.35 (t, 3H), 4.35 (q, 2H), 7.1 (s, 1H), 7.4 (m, 2H), 12.42 (bs, 1H); M/z (+) 258 (M$^+$), together with ethyl 5,6-dichloroindole-2-carboxylate in 30% yield (2 steps), mp 210–211°; NMR δ(CD$_3$SOCD$_3$) 1.35 (t, 3H), 4.35 (q, 2H), 7.15 (s, 1H), 7.6 (s, 1H), 12.14 (bs, 1H); M/z (+) 258 (M$^+$).

Ethyl 7-trifluoromethylindole-2-carboxylate in 22% yield (2 steps), mp 74–75°; NMR δ(CD$_3$SOCD$_3$) 1.35 (t, 3H), 4.35 (q, 2H), 7.25 (t, 1H), 7.35 (s, 1H), 7.6 (d, 1H), 7.95 (d, 1H) 11.9 (bs, 1H); M/z (+) 257 (M$^+$).

Ethyl 4-fluoroindole-2-carboxylate in 3% yield (2 steps); NMR δ(CD$_3$SOCD$_3$) 1.35 (t, 3H), 4.35 (q, 2H), 6.85 (t, 1H), 7.15 (s, 1H), 7.25 (m, 2H), 12.2 (bs, 1H); M/z (+) 207 (M$^+$) together with ethyl 6-fluoroindole-2-carboxylate in 3% yield (2 steps); NMR δ(CD$_3$SOCD$_3$) 1.35 (t, 3H), 4.35 (q, 2H), 6.95 (t, 1H), 7.15 (m, 2H), 7.65 (t, 1H), 11.9 (bs, 1H); M/z (+) 207 (M$^+$).

Ethyl 7-fluoroindole-2-carboxylate in 23% yield (2 steps), mp 131–132°; NMR δ(CD$_3$SOCD$_3$) 1.3 (t, 3H), 4.3 (q, 2H), 7.0 (m, 2H), 7.2 (m, 1H), 7.5 (m, 1H), 12.3 (bs, 1H); M/z (+) 207 (M$^+$).

Method C

Ethyl 3-bromoindole-2-carboxylate

Asolution of bromine (2.72 ml) in DMF was added dropwise over 10 mins to a solution of ethyl indole-2-carboxylate in DMF. The reaction was stirred for 30 mins, then poured into water to precipitate a pale yellow solid which was filtered off and recrystallized from ethyl acetate to give the desired starting material as white needles (10.2 g, 72%), mp 150–151°; NMR δ(CDCl$_3$) 1.44 (t, 3H), 4.45 (q, 2H), 7.22 (m, 1H), 7.38 (m, 2H), 7.66 (d, 1H), 9.27 (bs, 1H); M/z (−) 268 (M$^+$), 266, 196, 194.

The procedure described above was repeated using the appropriate indole. Thus was obtained the compound described below.

Methyl 3-bromo-5-chloroindole-2-carboxylate in 97% yield; NMR δ(CD$_3$SOCD$_3$) 3.91 (s, 3H), 7.36 (dd, 1H), 7.5 (d, 1H), 7.54 (d, 1H), 12.47 (bs, 1H); M/z (+) 291, 289 (MH$^+$).

Method D

Ethyl 3-chloroindole-2carboxylate

Ethyl 3-chloroindole-2-carboxylate (3 g) and phosphorous pentachloride (9 g) were heated at 90° C. for 1 hour. The mixture was then cooled to room temperature, poured into water and the resulting solid filtered purified by column chromatography using isohexane-20% ethyl acetate as eluent to give the desired end product as a white solid (1.25 g, 35%); NMR δ(CD$_3$SOCD$_3$) 1.3 (t, 3H), 4.4 (q, 2H), 7.2 (t, 1H), 7.35 (t, 1H), 7.45 (d, 1H), 7.6 (d, 1H), 12.5 (1H, bs); M/z (−) 222 (M–H$^+$).

The procedure described above was repeated using the appropriate indole. Thus was obtained the compound described below.

Ethyl 3-chloro-5-fluoroindole-2-carboxylate in 60% yield; NMR δ(CD$_3$SOCD$_3$) 1.35 (t, 3H), 4.36 (q, 2H), 7.22 (t, 1H), 7.34 (dd, 1H), 7.48 (dd, 1H), 12.22 (1H, bs); M/z (+) 244 (MH$^+$), 242.

Method E

Isopropyl 3-methylindole-2-carboxylate

Sodium borohydride (0.23 g) was added to a stirred solution of ethyl 3-formylindole-2-carboxylate (0.2 g) and 10% palladium on carbon (0.11 g) in isopropanol (45 ml). The solution was heated at reflux for 4 hours, cooled and filtered through Celite. The solution was partitioned between ethyl acetate and water. Combined organic extracts were dried (MgSO$_4$) and concentrated in vacuo and the residue purified by column chromatography using isohexane-10% ethyl acetate as eluent to give the desired end product as a white solid (0.05 g, 25%); NMR δ(CD$_3$SOCD$_3$) 1.3 (d, 6H), 2.5 (s, 3H), 5.2 (m, 1H), 7.0 (m, 1H), 7.2 (m, 1H), 7.4 (m, 1H), 7.6 (d, 1H), 11.3 (bs, 1H).

Method F

Ethyl 3-acetylindole-2-carboxylate, ethyl 5-acetylindole-2-carboxylate and ethyl 7-acetylindole-2-carboxylate Acetyl chloride (0.76 ml) was added to a suspension of anhydrous aluminium (III) chloride (1.42 g) in 1,2-dichloroethane (20 ml) at 0° C. The reaction was stirred for 5 minutes then a solution of ethyl indole-2-carboxylate (1 g) in 1,2-dichloroethane (20 ml) was added dropwise over 10 minutes. The reaction was heated at reflux for 1 hour, cooled and poured into ice/water. The solution was partitioned between ethyl acetate and saturated aqueous sodium-hydrogen carbonate solution. Combined organic extracts were dried (MgSO$_4$) and concentrated in vacuo and the residue purified by column chromatography using isohexane-10% ethyl acetate as eluent to give firstly ethyl 7-acetylindole-2-carboxylate as a white solid (0.1 8 g, 15%); NMR δ(CD$_3$SOCD$_3$) 1.35 (t, 3H), 2.7 (s, 3H), 4.4 (q, 2H), 7.3 (m, 2H), 8.05 (m, 2H), 10.7 (bs, 1H); M/z (+) 232 (MH$^+$), followed by ethyl 3-acetylindole-2-carboxylate as a white solid (0.2 g, 16%); NMR δ(CD$_3$SOCD$_3$) 1.35 (t, 3H), 2.6 (s, 3H), 4.4 (q, 2H), 7.2 (t, 1H), 7.3 (t, 1H), 7.5 (d, 1H), 7.9 (d, 1H), 12.4 (bs, 1H); M/z (+) 232 (MH$^+$), followed by ethyl 5-acetylindole-2-carboxylate as a white solid (0.5 g, 42%); NMR δ(CD$_3$SOCD$_3$) 1.35 (t, 3H) 12.6 (s, 3H), 4.35 (q, 2H), 7.3 (s, 1H), 7.5 (d, 1H), 8.4 (s, 1H), 12.2 (bs, 1H); M/z (+) 232 (MH$^+$).

Method G

Methyl 4-hydroxyindole-2carboxylate

Boron tribromide (73.1 ml, 1.0 M solution in DCM) was added dropwise to a solution of methyl 4-methoxyindole-2carboxylate (5 g) in DCM (200 ml) cooled to −78° C. under argon. The reaction was allowed to warm to room temperature then partitioned between dichloromethane and saturated aqueous sodium hydrogen carbonate solution. Combined organic extracts were dried (MgSO$_4$) and concentrated in vacuo and the residue purified by column chromatography using isohexane-50% ethyl acetate as eluent to give the end product as a yellow solid (2.98 g, 64%); NMR δ(CD$_3$SOCD$_3$) 3.82 (s, 3H), 6.36 (d, 1H), 6.85 (d, 1H), 7.02 (t, 1H), 7.17 (d, 1H), 9.66 (s, 1H), 11.72 (bs, 1H); M/z (+) 192 (MH$^+$).

Method H

Methyl 4-acetoxyindole-2-carboxylate

Methyl 4-hydroxyindole-2-carboxylate (0.5 g) and 4-dimethylaminopyridine (50 mg) were dissolved in acetic anhydride (5 ml) and heated at 80° C. for 3 hours. The reaction was allowed to cool overnight to precipitate white crystals, which were filtered and dried in vacuo (0.44 g, 72%); NMR δ(CD$_3$SOCD$_3$) 2.34 (s, 3H), 3.85 (s, 3H), 6.80 (d, 1H) 7.06 (s, 1H), 7.23 (t, 1H), 7.29–7.35 (m, 1H), 12.1 (bs, 1H); M/z (−) 232 (M−H$^+$).

Method I

Methyl N-(3,4dichlorobenzyl)4-hydroxyindole-2-carboxylate

Sodium methoxide (92 mg) was added to methyl 4-acetoxy-N-(3,4-dichlorobenzyl)indole-2-carboxylate in methanol (10 ml) and the reaction stirred for 4 hours. The reaction was then acidified with 2 M HCl to precipitate a white solid which was filtered and dried in vacuo (0.21 g, 77%); NMR δ(CD$_3$SOCD$_3$) 3.80 (s, 3H), 5.74 (s, 2H), 6.45 (d, 1H), 6.75–6.82 (m, 1H), 6.95 (d, 1H), 7.04–7.15 (m, 2H), 7.30 (m, 1H), 7.41 (s, 1H) 9.89 (s, 1H); M/z (+) 318 (MH$^+$). The procedure described above was repeated using the appropriate indole. Thus were obtained the compounds described below.

Methyl N-(4chlorobenzyl)4-hydroxyindole-2-carboxylate in 77% yield; NMR δ(CD$_3$SOCD$_3$) 3.79 (s, 3H), 5.76 (s, 2H), 6.45 (d, 1H), 6.94 (d, 1H), 7.01 (d, 2H), 7.1 (t, 1H), 7.30 (d, 1H), 7.4 (s, 1H),9.89 (s, 1H); M/z (+) 318 (MH$^+$), 316.

Methyl N-(3-chlorobenzyl)-4-hydroxyindole-2-carboxylate in 94% yield; NMR δ(CD$_3$SOCD$_3$) 3.8 (s, 3H), 5.78 (s, 2H), 6.45 (d, 1H), 6.9–6.96 (m, 2H), 7.03–7.14 (m, 2H), 7.41 (s, 1H), 9.9 (s, 1H); M/z (+) 318 (MH$^+$), 316.

Method J

Ethyl 4-aminoindole-2-carboxylate

Ethyl 4-nitroindole-2-carboxylate (2.3 g) and 10% palladium on carbon (0.5 g) in ethanol (400 ml) were stirred under a hydrogen atmosphere for 3 hours. The reaction was then filtered through Celite and concentrated to give the end product as a pale brown solid (1.4 g, 70%); NMR δ(CD$_3$SOCD$_3$) 1.3 (t, 3H), 4.3 (q, 2H), 5.4 (s, 2H), 6.1 (d, 1H), 6.6 (d, 1H), 6.9 (dd, 1H), 7.3 (s, 1H), 11.4 (bs, 1H); M/z (+) 205 (MH$^+$).

What we claim is:

1. A method for antagonising an MCP-1 mediated effect in a warm-blooded animal in need thereof comprising administering to said animal an antagonising-effective amount of a compound of the formula (I):

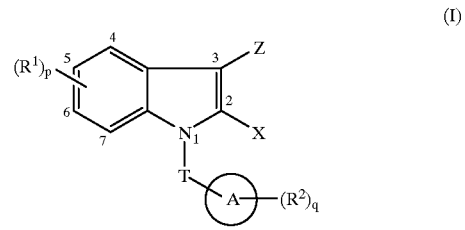

(I)

wherein

R$^1$ is independently selected from trifluoromethyl, C$_{1-4}$alkyl, halo, hydroxy, C$_{1-4}$alkoxy, C$_{1-4}$alkanoyl, C$_{1-4}$alkanoyloxy, amino, cyano, C$_{1-4}$alkylamino, di(C$_{1-4}$alkyl)amino, C$_{1-4}$alkanoylamino, nitro, carbamoyl, C$_{1-4}$alkoxycarbonyl, thiol, C$_{1-4}$alkylsulphanyl, C$_{1-4}$alkylsulphinyl, C$_{1-4}$alkylsulphonyl, sulphonamido, carbamoyl C$_{1-4}$alkyl, N—(C$_{1-4}$alkyl)carbamoylC$_{1-4}$alkyl, N—(C$_{1-4}$alkyl)$_2$carbamoyl-C$_{1-4}$alkyl, hydroxy C$_{1-4}$alkyl, C$_{1-4}$alkoxy C$_{1-4}$alkyl, morpholino, pyrrolidinyl, carboxy C$_{1-4}$alkylamino, R$^3$ and —OR$^3$, where R$^3$ is optionally substituted aryl or an optionally substituted 5- or 6-membered heteroaryl ring;

p is 0–4 and R$^1$ can have the same or different values when p is 2–4 with the proviso that no more than one R$^1$ can be chosen from the group amino, C$_{1-4}$alkylamino, di(C$_{1-4}$alkyl)amino, morpholino and pyrrolidinyl;

T is of the formula

—(CHR$^4$)$_m$—, where R$^4$ is independently selected from hydrogen or C$_{1-4}$alkyl and m=1–3 and R$^4$ can have different values when m is 2 or 3;

X is CO$_2$R$^4$, SO$_3$H, cyano, —SO$_2$NHR$^4$, —SO$_2$NHAr, or —CONHR$^5$ wherein:

R$^4$ is as defined above;

Ar is an optionally substituted phenyl or optionally substituted 5 or 6 membered heteroaryl ring; and R$^5$ is H, cyano, C$_{1-4}$alkyl, OH, —SO$_2$—C$_{1-4}$alkyl, —SO$_2$CF$_3$, or —SO$_2$-phenyl, or R$^5$ is —(CHR$^4$)$_r$—COOH where r is 1–3 and each R$^4$ can take a different value, as defined above, when r is 2–3;

A is selected from phenyl, naphthyl, furyl, pyridyl and thienyl;

R$^2$ is independently selected from trifluoromethyl, C$_{1-4}$alkyl, halo, hydroxy, CF$_3$O—, C$_{1-4}$alkoxy, C$_{1-4}$alkanoyl, C$_{1-4}$alkanoyloxy, amino, cyano, C$_{1-4}$alkylamino, (C$_{1-4}$alkyl)$_2$amino, C$_{1-4}$alkanoylamino, nitro, carboxy, carbamoyl, C$_{1-4}$alkoxycarbonyl, thiol, C$_{1-4}$alkylsulphanyl, C$_{1-4}$alkylsulphinyl, C$_{1-4}$alkylsulphonyl, sulphonamido, carbamoylC$_{1-4}$alkyl, N—(C$_{1-4}$alkyl) carbamoylC$_{1-4}$alkyl, N—(C$_{1-4}$alkyl)$_2$ carbamoyl-$C_{1-4}$alkyl, hydroxy$C_{1-4}$alkyl, $C_{1-4}$alkoxy$C_{1-4}$alkyl or two $R^2$ values together may form a divalent radical of the formula —O(CH$_2$)$_{1-4}$O— attached to adjacent carbon atoms on ring A;

q is 0–4 and $R^2$ can have the same or different values when q is 2–4;

Z is hydrogen, fluoro, chloro, bromo, iodo, methyl, trifluoromethyl, hydroxymethyl, carboxy$C_{3-6}$cycloalkyl or;

Z is —(CHR$^4$)$_r$—NR$^6$R$^7$, where r is 0–2, $R^6$ and $R^7$ are independently selected from H and $C_{1-4}$alkyl, or $R^6$ and $R^7$ together with the nitrogen to which they are attached form a 5 or 6 membered non-aromatic ring optionally containing one further heteroatom selected from O, N or S;

or a pharmaceutically acceptable salt or an in vivo hydrolysable ester thereof.

2. A method for the treatment of a disease or medical condition mediated by MCP-1 comprising administering to a warm-blooded animal in need thereof a treatment-effective amount of a compound of the formula (I):

(I)

wherein
$R^1$ is independently selected from trifluoromethyl, $C_{1-4}$alkyl, halo, hydroxy, $C_{1-4}$alkoxy, $C_{1-4}$alkanoyl, $C_{1-4}$alkanoyloxy, amino, cyano, $C_{1-4}$alkylamino, di($C_{1-4}$alkyl)amino, $C_{1-4}$alkanoylamino, nitro, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl $C_{1-4}$alkyl, N—($C_{1-4}$alkyl)carbamoyl$C_{1-4}$alkyl, N—($C_{1-4}$alkyl)$_2$carbamoyl-$C_{1-4}$alkyl, hydroxy $C_{1-4}$alkyl, $C_{1-4}$alkoxy $C_{1-4}$alkyl, morpholino, pyrrolidinyl, carboxy $C_{1-4}$alkylamino, $R^3$ and —OR$^3$, where $R^3$ is optionally substituted aryl or an optionally substituted 5- or 6-membered heteroaryl ring;

p is 0–4 and $R^1$ can have the same or different values when p is 2–4 with the proviso that no more than one $R^1$ can be chosen from the group amino, $C_{1-4}$alkylamino, di($C_{1-4}$alkyl)amino, morpholino and pyrrolidinyl;

T is of the formula

—(CHR$^4$)$_m$—, where
$R^4$ is independently selected from hydrogen or $C_{1-4}$alkyl and m=1–3 and $R^4$ can have different values when m is 2 or 3;

X is CO$_2$R$^4$, SO$_3$H, cyano, —SO$_2$NHR$^4$, —SO$_2$NHAr, or —CONHR$^5$; wherein
$R^4$ is as defined above;
Ar is an optionally substituted phenyl or optionally substituted 5 or 6 membered heteroaryl ring;
$R^5$ is H, cyano, $C_{1-4}$alkyl, OH, —SO$_2$—$C_{1-4}$alkyl, —SO$_2$CF$_3$, —SO$_2$-phenyl, or $R^5$ is —(CHR$^4$)$_r$— COOH where r is 1–3 and each $R^4$ can take a different value, as defined above, when r is 2–3;

A is selected from phenyl, naphthyl, furyl, pyridyl and thienyl;

$R^2$ is independently selected from trifluoromethyl, $C_{1-4}$alkyl, halo, hydroxy, CF$_3$O—, $C_{1-4}$alkoxy, $C_{1-4}$alkanoyl, $C_{1-4}$alkanoyloxy, amino, cyano, $C_{1-4}$alkylamino, ($C_{1-4}$alkyl)$_2$amino, $C_{1-4}$alkanoylamino, nitro, carboxy, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—($C_{1-4}$alkyl)carbamoyl $C_{1-4}$alkyl, N—($C_{1-4}$alkyl)2carbamoyl-$C_{1-4}$alkyl, hydroxy$C_{1-4}$alkyl, $C_{1-4}$alkoxy$C_{1-4}$alkyl or two $R^2$ values together may form a divalent radical of the formula —O(CH$_2$)$_{1-4}$O— attached to adjacent carbon atoms on ring A;

q is 0–4 and $R^2$ can have the same or different values when q is 2–4;

Z is hydrogen, fluoro, chloro, bromo, iodo, methyl, trifluoromethyl, hydroxymethyl, carboxy $C_{3-6}$cycloalkyl, or Z is —(CHR$^4$)$_r$—NR$^6$R$^7$, where r is 0–2, $R^6$ and $R^7$ are independently selected from H and $C_{1-4}$alkyl or $R^6$ and $R^7$ together with the nitrogen to which they are attached form a 5 or 6 membered non-aromatic ring optionally containing one further heteroatom selected from O, N or S;

or a pharmaceutically acceptable salt or an in vivo hydrolysable ester thereof.

3. The method of claim 2 wherein the disease or medical condition is selected from rheumatoid arthritis, glomerular nephritides, lung fibrosis, restenosis, alveolites, asthma, atherosclerosis, psoriasis, delayed-type hypersensitivity reactions of the skin, inflammatory bowel disease, multiple sclerosis, brain trauma, stroke, reperfusion injury, ischemia, myocardial infarction and transplant rejection.

4. The method as claimed in claim 1 or claim 2 wherein the compound of formula I is a compound of formula (I'):

(I')

wherein
$R^e$ is methoxy, fluoro, chloro, bromo, nitro, amino, phenoxy or trifluoromethyl;

x is 1 or 2 with the proviso that there is at most one methoxy group;

X' is carboxy, —CONHSO$_2$CF$_3$, —CONHEt or —CONHMe;

A' is phenyl or thienyl;

$R^f$ is chloro, bromo, methyl, methoxy, nitro, trifluoromethyl or trifluoromethoxy;

y is 1 or 2;

Z' is hydrogen, methyl, bromo or carboxycyclopropyl;

or a pharmaceutically acceptable salt or in vivo hydrolysable ester thereof.

5. The method as claimed in claim 4 wherein A'(R$^f$)$_y$ is 3-chlorophenyl, 4-chlorophenyl, or 3,4-dichlorophenyl.

6. The method as claimed in claim 4 wherein X' is carboxy.

7. A compound of the formula (A):

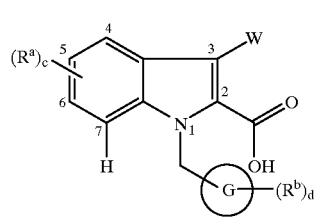

(A)

wherein $R^a$ is 4-methoxy, 4-phenyl, 4-amino, 4-thien-2-yl, 5-chloro, 5-methoxy, 5-nitro, 5-bromo, 5-phenoxy, 5-fluoro, 5-carboxymethylamino, 5-amino, 6-fluoro, 6-trifluoromethyl, 6-nitro or 6-chloro;

c is 0, 1 or 2 provided that there is no more than one methoxy group;

W is hydrogen, bromo, methyl or transcyclopropyl-2-carboxylic acid;

G is phenyl or thien-2-yl;
when G is phenyl $R^b$ is 3-chloro, 3-trifluoromethyl, 3-nitro, 3-methoxy, 4-trifluoromethyl, 4-trifluoromethoxy or 4-chloro;
when G is thien-2-yl $R^b$ is 5-chloro;

d is 1 or 2;

or a pharmaceutically acceptable salt or an in vivo hydrolysable ester thereof.

8. A compound selected from:

N-(3,4-Dichlorobenzyl)-5-nitroindole-2-carboxylic acid;
N-(3-Methylbenzyl)-5-nitroindole-2-carboxylic acid;
N-(3-Chlorobenzyl)-5-nitroindole-2-carboxylic acid;
5-Nitro-N-(3-trifluoromethylbenzyl)-indole-2-carboxylic acid;
5-Fluoro-N-(3-trifluoromethylbenzyl)indole-2-carboxylic acid;
6-Fluoro-N-(3-trifluoromethylbenzyl)indole-2-carboxylic acid;
3-Bromo-N-(3-trifluoromethylbenzyl)indole-2-carboxylic acid;
N-(3,4-Dichlorobenzyl)-4-(thien-2-yl)indole-2-carboxylic acid;
N-(3,4-Dichlorobenzyl)-3-(trans-2-carboxy-cyclopropyl) indole-2-carboxylic acid;
5-Chloro-N-(3,4-dichlorobenzyl)indole-2-carboxylic acid;
6-Chloro-N-(3,4-dichlorobenzyl)indole-2-carboxylic acid; and
N-(3,4-Dichlorobenzyl)-4-methoxyindole-2-carboxylic acid;

and pharmaceutically acceptable salts and in vivo hydrolysable esters thereof.

9. The method as claimed in claim 1 or claim 2 wherein $A(R^2)_q$ is 3-chlorophenyl, 4-chlorophenyl or 3,4-dichlorophenyl.

10. The method as claimed in claim 1 or claim 2 wherein X is carboxy.

11. A compound of the formula (I'):

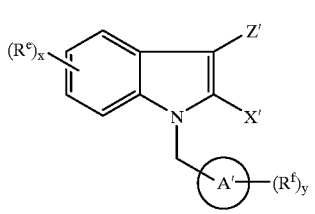

(I')

wherein
$R^e$ is methoxy, fluoro, chloro, bromo, nitro, amino, phenoxy or trifluoromethyl;
x is 1 or 2 with the proviso that there is at most one methoxy group;
X' is carboxy;
A' is phenyl;
$R^f$ is chloro, bromo, methyl, methoxy, trifluoromethyl or trifluoromethoxy;
y is 1 or 2; and
Z' is hydrogen;
or a pharmaceutically acceptable salt or in vivo hydrolysable ester thereof.

12. A compound of the formula (I'):

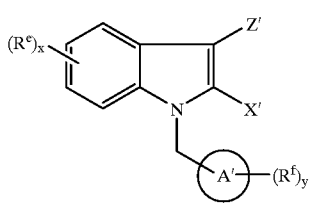

(I')

wherein
$R^e$ is methoxy, fluoro, chloro, bromo, nitro, amino, phenoxy or trifluoromethyl;
x is 1 or 2 with the proviso that there is at most one methoxy group;
X' is carboxy;
A' is phenyl;
$R^f$ is chloro, bromo, methyl, methoxy, nitro, trifluoro methyl or trifluoromethoxy;
y is 2; and
Z' is hydrogen;
or a pharmaceutically acceptable salt or in vivo hydrolysable ester thereof.

13. A compound of the formula (I):

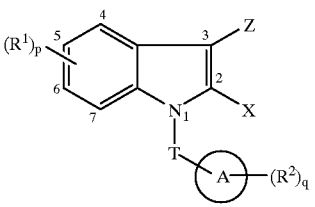

(I)

wherein
$R^1$ is independently selected from trifluoromethyl, $C_{1-4}$alkyl, halo, hydroxy, $C_{1-4}$alkoxy, $C_{1-4}$alkanoyl, $C_{1-4}$alkanoyloxy, amino, cyano, $C_{1-4}$alkylamino, di($C_{1-4}$alkyl)amino, $C_{1-4}$alkanoylamino, nitro, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl $C_{1-4}$alkyl, N—($C_{1-4}$alkyl)carbamoyl$C_{1-4}$alkyl, N—($C_{1-4}$alkyl)$_2$carbamoyl-$C_{1-4}$alkyl, hydroxy $C_{1-4}$alkyl, $C_{1-4}$alkoxy$C_{1-4}$alkyl, morpholino, pyrrolidinyl, carboxy$C_{1-4}$alkylamino, $R^3$ and —$OR^3$, where $R^3$ is optionally substituted phenyl or an optionally substituted 5- or 6-membered heteroaryl ring;

p is 1 or 2, and $R^1$ can have the same or different values when p is 2 with the proviso that no more than one can be chosen from the group amino, $C_{1-4}$alkylamino, di($C_{1-4}$alkyl)amino, morpholino and pyrrolidinyl;

Z is hydrogen;

X is carboxy;

T is —$CH_2$—;

A is phenyl;

$R^2$ is independently selected from chloro, bromo, methyl, methoxy, nitro, trifluoromethyl and trifluoromethoxy;

q is 2;

the positions ortho to T on the phenyl ring A are unsubstituted; and position 7 of the indole ring is unsubstituted;

or a pharmaceutically acceptable salt or an in vivo hydrolysable ester thereof.

14. The method as claimed in claim 1 or in claim 2 wherein $R^1$ is independently selected from trifluoromethyl, $C_{1-4}$alkyl, halo, hydroxy, $C_{1-4}$alkoxy, $C_{1-4}$alkanoyl, $C_{1-4}$alkanoyloxy, amino, cyano, $C_{1-4}$alkylamino, di($C_{1-4}$alkyl)amino, $C_{1-4}$alkanoylamino, nitro, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl $C_{1-4}$alkyl, N—($C_{1-4}$alkyl)carbamoyl$C_{1-4}$alkyl, N—($C_{1-4}$alkyl)$_2$carbamoyl-$C_{1-4}$alkyl, hydroxy $C_{1-4}$alkyl, $C_{1-4}$alkoxy$C_{1-4}$alkyl, morpholino, pyrrolidinyl, carboxy$C_{1-4}$alkylamino, $R^3$ and —$OR^3$, where $R^3$ is optionally substituted phenyl or an optionally substituted 5- or 6-membered heteroaryl ring;

p is 1 or 2, and $R^1$ can have the same or different values when p is 2 with the proviso that no more than one can be chosen from the group amino, $C_{1-4}$alkylamino, di($C_{1-4}$alkyl)amino, morpholino and pyrrolidinyl;

Z is hydrogen;

X is carboxy;

T is —$CH_2$—;

A is phenyl;

$R^2$ is independently selected from chloro, bromo, methyl, methoxy, nitro, trifluoromethyl and trifluoromethoxy;

q is 2;

the positions ortho to T on the phenyl ring A are unsubstituted; and position 7 of the indole ring is unsubstituted;

or a pharmaceutically acceptable salt or an in vivo hydrolysable ester thereof.

15. A pharmaceutical composition which comprises a compound as claimed in any one of claims 7, 8, 11, 12 or 13 or a pharmaceutically acceptable salt or an in vivo hydrolysable ester thereof, together with a pharmaceutically acceptable diluent or carrier.

* * * * *

UNITED STATES PATENT AND TRADEMARK OFFICE
CERTIFICATE OF CORRECTION

PATENT NO. : 6,441,004 B1
DATED : August 27, 2002
INVENTOR(S) : Faull et al.

It is certified that error appears in the above-identified patent and that said Letters Patent is hereby corrected as shown below:

Title page,
Item [56], References Cited, FOREIGN PATENT DOCUMENTS, change
"0 144 014" to -- 0 114 014 --.

Column 44,
Line 33, change "aryl" to -- phenyl --.

Column 45,
Line 45, change "aryl" to -- phenyl --.

Signed and Sealed this

Eighth Day of February, 2005

JON W. DUDAS
*Director of the United States Patent and Trademark Office*